(12) United States Patent
Fang et al.

(10) Patent No.: US 6,556,199 B1
(45) Date of Patent: Apr. 29, 2003

(54) METHOD AND APPARATUS FOR FAST VOXELIZATION OF VOLUMETRIC MODELS

(75) Inventors: Shiaofen Fang, Carmel, IN (US); Hongsheng Chen, Indianapolis, IN (US)

(73) Assignee: Advanced Research and Technology Institute, Indianapolis, IN (US)

( * ) Notice: Subject to any disclaimer, the term of this patent is extended or adjusted under 35 U.S.C. 154(b) by 0 days.

(21) Appl. No.: 09/372,194

(22) Filed: Aug. 11, 1999

(51) Int. Cl.$^7$ .............................................. G06T 17/00
(52) U.S. Cl. ...................................................... 345/424
(58) Field of Search ................................ 345/424, 542, 345/545, 552, 426, 589, 629

(56) References Cited

U.S. PATENT DOCUMENTS

| | | | |
|---|---|---|---|
| 4,697,178 A | 9/1987 | Heckel | |
| 4,907,174 A | 3/1990 | Priem | |
| 4,988,985 A | * 1/1991 | Barkans et al. | 345/545 |
| 5,038,302 A | 8/1991 | Kaufman | |
| 5,469,535 A | 11/1995 | Jarvis et al. | |
| 5,566,279 A | 10/1996 | Katayama | |
| 5,570,460 A | * 10/1996 | Ramanujam | 345/424 |
| 5,579,455 A | 11/1996 | Greene et al. | |
| 5,594,842 A | 1/1997 | Kaufman et al. | |
| 5,644,689 A | 7/1997 | Ban et al. | |
| 5,760,781 A | 6/1998 | Kaufman et al. | |
| 6,184,891 B1 | * 2/2001 | Blinn | 345/426 |
| 6,246,422 B1 | * 6/2001 | Emberling et al. | 345/552 |

OTHER PUBLICATIONS

Shareef et al., "Rapid Previewing Via Volume–Based Solid Modeling", 1995.*

Lacroute et al., "Fast Volume Rendering Using a ShearWarp Factorization of the Viewing Transformation", 1994.*

Glinert, Susan, evaluation of Deneba Software's Canvas for Windows paint software, Computer Shopper, v14, n4, p. 446 (Apr. 1994).*

Arie E. Kaufman, Volume Visualization: Principles and Advances, Center for Visual Computing and Computer Science Department, SUNY, (no date).

* cited by examiner

*Primary Examiner*—Almis R. Jankus
*Assistant Examiner*—Lance W. Sealey
(74) *Attorney, Agent, or Firm*—Ice Miller; Thomas A. Walsh; Doreen J. Gridley

(57) ABSTRACT

The present invention relates to an apparatus and method for voxelizing geometric and volumetric models of objects in 3D space, i.e. converting these 3D models into a voxel-based volume representation. Based on an unconventional way of using the 3D graphics hardware in modern graphics workstations, the present invention generates slices of the model as frame buffer images, and then stores the slices in a 3D texture memory for interactive volume rendering. Since most of the computation is carried out directly by hardware, the voxelization algorithms of the present invention are much faster than existing algorithms, and are able to achieve interactive volume rendering and manipulation of complex 3D scenes consisting of intermixed geometric models and sampled volume data sets (e.g. CT and MRI scans). As a result, the present invention significantly enhances the capabilities of volume-based techniques (volume visualization and volume graphics) for large-scale 3D applications such as surgical planning and simulation, CAD/CAM and computer animation.

20 Claims, 27 Drawing Sheets

300 — PROCEDURE SurfaceVoxelization (int N)
BEGIN

302 —
```
/*Initialize display environment */
Create a window of size NxN;
Define a 3D texture object of size NxNxN;
Define desired lighting and texturing;
Enable polygon anti-aliasing and line anti-aliasing;
```

304 —
```
/* Setting the slicing parameters */
Compute the bounding box of the scene;
zplane1 = Z value of the front face of the bounding box;
zstep = bounding_box_size / N;
```

306 —
```
/* Slicing loop */
FOR (i = 1 to N)
BEGIN
   zplane2 = zplane1 + zstep;
   Define the thin orthogonal viewing volume;
   Clear frame buffer;

/* Fill all surfaces */
   Display all surfaces in FILLED mode;

/* Draw curves and polygon edges */
   Display all curves and all surfaces in WIRE_FRAME mode;

*Write frame buffer to 3D texture memory;
   zplane1 = zplane2
END
```

FIG. 10

```
PROCEDURE SolidVoxelization (int N)
BEGIN
```

312
```
/* initialization */
Create a window of size NxN;
Define a 3D texture object of size NxNxN;
Compute the bounding box of the solid;
```

314
```
/* Initialize display parameters for solid voxelization */
Set object color to (255, 255, 255);
Set background color to (0, 0, 0);
Clear frame buffer;
Set the "XOR" blending function;
```

316
```
/* Generate the solid volume */
FOR (each slice)
BEGIN
  Define the thin orthogonal viewing volume;
  Display all surfaces in FILLED mode;
  Write frame buffer to 3D texture memory;
END
```

318
```
/* Super-impose the surfaces */
Define desired lighting and texturing;
Enable polygon anti-aliasing and line anti-aliasing;
FOR (each slice)
BEGIN
  Define the thin orthogonal viewing volume;
  Clear frame buffer;
  Display all surfaces in FILLED mode;
  Display all surfaces in WIRE_FRAME mode;

/*merge with the solid volume */
  Set the "OR" blending function;
  Draw Z-plane by 3D texture mapping with the solid volume;
  Disable blending function;

Write frame buffer back to the texture object;
END
```

| No. | (VOXEL) | SLICE ELEMENT | PIXEL X OR COLOR VALUE |
|---|---|---|---|
| 0 | 614 | E | (0,0,0) |
| 1 | 608 | F | (255,255,255) |
| 2 | 612 | E | (255,255,255) |
| 3 | 612 | E | (255,255,255) |
| 4 ⋮ | 612 | E | (255,255,255) |
| N−1 | 612 | E | (255,255,255) |
| N | 610 | F | (0,0,0) |
| N+1 | 615 | E | (0,0,0) |

FIG. 13

```
PROCEDURE CSG_Voxelization (CSG_NODE root)
BEGIN
```

730

742 — Generate a cumulative transformation matrix for each primitive;

744 — Define texture objects for all volume primitives;

746 — Assign color codes to all primitives;

748 — pcm = CSG_PCM (root);
Clear frame buffer;

752 —
```
FOR (each z_plane)
BEGIN
  Define the thin viewing volume;
  FOR (each primitive)
  BEGIN
    Define system transformation matrix;
    IF (geometric primitive)
      Set the XOR blending function;
      Set the primitive's color;
      Render the primitive;
    ELSE
      Clear the frame buffer's color bit
        for this primitive;
      Bind 3D texture;
      Set color look-up table;
      Set the OR blending function;
      Draw Z-plane by 3D texture mapping;
    ENDIF
END
```

754 — Define frame buffer pixel map using pcm;

756 — Copy frame buffer to texture memory;

END
END

FIG. 23

```
PCM PROCEDURE CSG_PCM (CSG_NODE N)
BEGIN

IF (N is a leaf node)
        RETURN the primitive PCM;
    ELSE
        PCM_left = CSG_PCM (N.left);
        PCM_right = CSG_PCM (N.right);
        PCM_combined =
            combine (PCM_left, PCM_right, N.op);
        RETURN PCM_combined;
    ENDIF

END
```

FIG. 24

BOOLEAN OPERATIONS FOR POINT-CLASSIFICATION

| OP C1\C2 | UNION | | INTERSECTION | | SUBTRACTION | |
|---|---|---|---|---|---|---|
| | 1 | 0 | 1 | 0 | 1 | 0 |
| 1 | 1 | 1 | 1 | 0 | 0 | 1 |
| 0 | 1 | 0 | 0 | 0 | 0 | 0 |

METHOD AND APPARATUS FOR FAST VOXELIZATION OF VOLUMETRIC MODELS

A portion of the disclosure of this patent document contains material which is subject to copyright protection. The copyright owner has no objection to the facsimile reproduction by anyone of the patent document or the patent disclosure, as it appears in its Patent and Trademark Office patent file or records, but otherwise reserves all copyright rights whatsoever.

BACKGROUND OF THE INVENTION

1. Field of the Invention

The present invention relates generally to a method and apparatus for converting three dimensional data and computer models into discrete representations and displaying the resulting discrete representation on a two-dimensional display, and more particularly to a method and apparatus for real-time voxelization of three dimensional data and subsequent real-time volume rendering.

2. Related Art

Broadly speaking, three-dimensional (3D) objects tend to have different characteristics depending on their origins as either synthetic objects or empirical objects. Typical synthetic objects include computer-aided design (CAD) models, computer-aided manufacturing (CAM) models and other computer-spawned entities. Typical empirical objects include computerized tomography (CT) and magnetic resonance imaging (MRI) 3D images formed from two-dimensional (2D) "slices" of empirical measurements. Typically, synthetic 3D objects are represented as 3D models. These 3D models typically reside in the memory of a computer, such as a graphics workstation or a personal computer. Typically, empirical objects are represented as volume data. These volume data typically reside in an embedded controller or computer in the device that obtained the data or in a separate computer such as a workstation or a personal computer. In many real world applications, these two types of objects need to interact (e.g., in a medical simulation where a body part is represented by empirical MRI volume data while the "scalpel" is a synthetic model). Typically, the results of their interaction need to be displayed on a 2D monitor. (The process of displaying a 3D object in 2D space is called rendering.)

Volume data are 3D objects from many possible sources, including synthetic objects (e.g., a CAD model) or "real world" objects, such as a sequence of CT or MRI slices. In operation, data representing the volumetric objects is stored in a volume buffer of voxels (the 3D analog to pixels in 2D). Typically volume data are used to manipulate, render and display 3D objects in two related areas, volume graphics and volume visualization. Volume graphics deals with the synthesis, modeling, manipulation, rendering and display of volumetric geometric objects. Volume visualization uses interactive graphics and imaging to extract and display useful information from volumetric data.

Recent advances in volume visualization and volume-based graphics techniques have made volume graphics a potential new paradigm for the next generation computer graphics technology. One of the main obstacles for volume graphics to achieve this goal, however, is its limited support to the modeling operations of volumetric and geometric objects.

Historically, the need for direct interaction with 3D objects, such as interactive object manipulations and design, has been an important driving force for modern 3D computer graphics. A very rich set of surface graphics techniques and algorithms have been developed to provide interactive graphical display support for applications such as solid modeling and animation. In order to achieve and even surpass the capabilities of traditional surface graphics, volume graphics needs to provide efficient rendering support for applications involving dynamic volumetric scenes and interactive manipulations and operations of volumetric and geometric objects. A good background discussion of the field of volume visualization are the seminar notes found in "Volume Visualization: Principles and Advances" by Dr. Arie E. Kaufman, Center for Visual Computing and Computer Science Department, State University of New York at Stony Brook, August, 1997, and incorporated herein by reference.

There are two main approaches to displaying volumetric 3D objects on a 2D display, surface rendering and volume rendering. Surface rendering uses geometric primitives to approximate a surface contained in the volumetric data. The geometric primitives can then be rendered (i.e., turned into 2D images) using conventional graphics accelerator hardware. This approach, however, has a few significant drawbacks. First, the use of geometric primitives is only an approximation, and one that may require a prohibitive number of such primitives to adequately approximate the object represented by the volumetric data. Moreover, certain objects (e.g., clouds, and fog) cannot be adequately represented using geometric primitives. Second, since the geometric primitives represent only the surface of the object, the geometric primitives do not convey any information contained within the object.

In contrast, volume rendering converts volumetric data directly into a 2D image, without the intermediate step of generating geometric primitives. This approach overcomes the disadvantages of the surface rendering approach outlined above, including preserving the volumetric data within the object. At present there are a number of volume rendering techniques that approach real time speeds through a combination of commercially available graphics Applications Programming Interface (API) software and graphics accelerator hardware.

In a volume representation, a scalar volume is a scale field sampled over a 3D regular grid in a regular volume space. A scalar value (i.e., intensity) is defined at each grid point representing a certain property (e.g., density) of the object at this point. The small cuboid formed by eight neighboring grid points is called a voxel. Thus, the intensity value of any point within a voxel can be obtained by trilinear interpolation from the eight vertices of the voxel. A binary volume is a volume having only 0 or 1 intensity values, with 1 representing a point inside an object and 0 representing a background point (i.e., a point outside the object).

The process of converting a 3D model into a volume representation is called voxelization. Conceptually voxelization (i.e., 3D scan conversion) can be considered as a set membership classification problem for all voxels in a regular volume against the given 3D model. It can also be considered as a 3D extension of the 2D scan conversion process, such as the polygon scan conversion algorithms widely used in computer graphics. Although hardware and software solutions for fast volume rendering have been developed for regular volume representations, voxelization algorithms that generate the volume representations from complex geometric and volumetric models are still too slow to support interactive modeling operations.

Several important theoretical issues have been addressed by experts in the computer graphics field. These issues include accuracy, separability (or tunnel-free) and minimality. However, the important issue of voxelization speed has heretofore received very little attention. As a result, existing voxelization algorithms, while generally adequate, are slow and not able to provide interactive feedback for object operations. In addition, existing algorithms are object-type specific. That is, a different algorithm needs to be employed for each different type of object (e.g., lines, circles, polygons, quadratic surfaces, etc.), making the implementation of a general volume graphics application difficult.

Broadly speaking, the existence of curve and surface voxelization algorithms aim to provide efficient ways to extend 2D scan conversion methods to a volumetric domain. This requires additional sampling in the third dimension for each scan line. One important difference between 2D scan conversion and voxelization is that voxelization is decoupled from the rendering process, and is therefore only done once each time the model is modified. Even so, fast voxelization is still a requirement for interactive systems where models can be modified interactively, and every model modification requires a re-voxelization.

Unlike curve/surface voxelization, the voxelization of solid objects has not been significantly studied. Early methods in solid modeling can generate the spatial enumeration representation for a solid object, which is essentially a solid voxelization process. But these are mostly brute-force algorithms and are far too slow for interactive applications. Surface voxelization methods do not generate the interior voxels that are necessary for the volumetric representation of solid objects. An algorithm disclosed by Dr. Arie Kaufman in his paper entitled, "Efficient algorithms for 3D scan-conversion of parametric curves, surfaces, and volumes" in SIGGRAPH '87, volume 21, pages 171–179, July 1987, can voxelize trivariate parametric polynomial volumes. But most solid objects cannot be represented by such regular shaped trivariate parametric polynomials.

The two solid representation methods that dominate the computer graphics industry are Boundary Representation ("B_Rep") and Constructive Solid Geometry ("CSG). A B_Rep solid object is difficult to voxelize since its interior is not explicitly defined. In fact, except for the expensive point-classification based approach proposed by Y. T. Lee and A. A. G. Requicha in their paper entitled, "Algorithms for computing the volume and other integral properties of solids," in SIGGRAPH '94, pages 451–458, 1994, there has not been any efficient voxelization algorithm for general B_Rep solid objects.

Graphics techniques for CSG models have been studied by many researchers. The CSG representation allows users to define complex 3D solid objects by hierarchically combining simple geometric primitives using Boolean operations and affine transformations, as described by A. A. G. Requicha in "Representation for rigid solids: Theory, methods and systems," Computing Surveys, 12(4):437–464, December 1980. CSG is a very popular and powerful solid modeling scheme, particularly for interactive object manipulations and design. Traditionally, the primitives used in a CSG construction process are defined by simple analytic objects, such as cubes, cylinders and spheres. Some recent CSG algorithms can also support primitives that are general solid models defined by their boundary surfaces.

A natural extension of the CSG method is to allow the intensity values of the volume datasets to be computed during Boolean operations. That is, objects are extracted from the volume datasets using intensity thresholding. Such models are called Volumetric-CSG models, or simply "VCSG" models, and are potentially useful for combining geometric and volumetric objects in one common modeling environment.

Display of CSG modeled objects cannot be accomplished directly by standard graphics workstations since such models lack explicit representation of surface boundaries. There are a number of voxelization and volume rendering techniques for CSG or VCSG models. These techniques include the Beam Oriented voxelization algorithm outlined by Naeem Shareef and Roni Yagel in an article entitled, "Rapid previewing via volume-based solid modeling," in Solid Modeling '95, p 281–292, May 1995, the volume sampling approach outlined by Sidney Wang and Arie Kaufman in an article entitled, "Volume-sampled 3D modeling," in IEEE computer Graphics and Application, 14:26–32, September 1994, the octree-based rendering algorithm outlined by Shiaofen Fang and R. Srinivasan in an article entitled, "Volumetric CSG—a model-based volume visualization approach," in Proceedings of the $6^{th}$ International Conference in Central Europe on Computer Graphics and Visualization," pp. 88–95, February 1998, and the distance volume algorithm outlined by David E. Breen, Sean Mauch and Ross T. Whitaker in an article entitled, "3D scan conversion of CSG models into distance volumes," in Proceedings of the IEEE/ACM Symposium on Volume Visualization, pp. 7–14, 1998. These algorithms typically reconstruct a volume for the entire CSG or VCSG model in some form, which is then rendered by a volume rendering algorithm. Current volume reconstruction algorithms for CSG or VCSG models are very slow, with most software implemented CSG display algorithms being too slow for interactive applications and the few interactive CSG rendering algorithms reported either require special purpose hardware or restrict the CSG model to only certain types of operations (between objects and primitives). This problem with speed becomes even more challenging with generalized CSG models, in which the operations and display of two or more different types of objects need to be combined within a common 3D environment. For these reasons, while the VCSG technique is generally adequate, it has not yet provided effective support to interactive volumetric modeling.

One approach to developing an interactive approach to displaying CSG and VCSG objects would explicitly extract the iso-surfaces from the volume data sets by using their thresholding parameters to convert the generalized CSG model into a regular geometric CSG model. At that point an existing CSG display algorithm could be used to perform rendering. This approach, however, would be relatively slow and difficult for two reasons. First, the process of iso-surface extraction is very time consuming. Second, the extracted iso-surfaces normally contain a relatively large number of polygons, which would be relatively difficult and expensive to render (as well as to operate).

Interactive object operations also require real-time rendering of volume representations. Volume rendering is a powerful technique of generating 2D images directly from volume data sets through semi-transparent rendering of both the surfaces and the internal structures of the volumetric objects. A large number of volume rendering algorithms has been developed. While these algorithms are generally adequate, they are not yet able to provide real-time volume rendering for typical-sized volumes (e.g., $256^3$).

Volume rendering using hardware-assisted 3D texture mapping is becoming an increasingly attractive option as 3D texture mapping hardware becomes more available, since it offers interactive rendering speed with reasonably good image quality. One example of this approach is the Volumizer application of OpenGL API by Silicon Graphics, Inc. In this approach, slices of the volume of the object parallel to the viewing plane are generated by 3D texture mapping and composited to the frame buffer in a back-to-front order to form the final image. That is, objects (such as synthetic objects) are rendered (sliced) directly to the frame buffer and that volume rendered using the depth buffer. This approach does render synthetic objects and volume objects together in a common 3D model, but the synthetic objects lack volumetric information. For instance, cutting through a solid object modeled in this fashion will result in an empty interior space.

There is therefore a need for an improved method and apparatus for voxelizing volumetric models.

SUMMARY OF THE INVENTION

The present invention relates to an apparatus and method for voxelizing geometric and volumetric models of objects in 3D space, i.e. converting these 3D models into a voxel-based volume representation. Based on an unconventional way of using the 3D graphics hardware in modern graphics workstations, the present invention generates slices of the model as frame buffer images, and then stores the slices in a 3D texture memory for interactive volume rendering. Since most of the computation is carried out directly by hardware, the voxelization algorithms of the present invention are much faster than existing algorithms, and are able to achieve interactive volume rendering and manipulation of complex 3D scenes consisting of intermixed geometric models and sampled volume data sets (e.g. CT and MRI scans). As a result, the present invention significantly enhances the capabilities of volume-based techniques (volume visualization and volume graphics) for large-scale 3D applications such as surgical planning and simulation, CAD/CAM and computer animation.

In accordance with one form of the present invention, the voxelization method of the present invention voxelizes a 3D object of predetermined 3D model type by first generating a slice of the 3D object and storing the slice in a frame buffer having blending functions. Each pixel of the frame buffer represents a voxel in the slice. In generating the slice, the method determines the type of 3D model of the object and applies predetermined frame buffer blending functions associated with that 3D model type to the voxels of each slice stored in the frame buffer. The slice is then written from the frame buffer to a plane location in a 3D memory storage matrix, with the plane location for the slice chosen to maintain the relative position of the slice to the object. The process of generating slices, storing them in the frame buffer, applying predetermined frame buffer blending functions, and storing the resulting slice in 3D memory storage matrix is repeated until the entire object has been voxelized.

In accordance with another form of the present invention, the voxelization method generates the slice directly from the surface fragments of the object within the slice without applying frame buffer blending functions, for objects determined to be curve/surface 3D model types.

In accordance with another form of the present invention, for objects determined to be boundary/surface 3D model types the voxelization method applies an XOR blending function to convey between successive slices the status of each voxel in the slice as either inside or outside of the object.

In accordance with another form of the present invention, for objects determined to be Volume Constructive Solid Geometry 3D model types, the voxelization method converts all primitives of the 3D object that are of boundary/surface 3D model type to volumes. For each binary node of the VCSG tree representing the 3D object, when creating the slices in the frame buffer, the voxelization method uses frame buffer functions to simulate the Boolean operation required at that node.

In accordance with another form of the present invention, for objects of Generalized Constructive Solid Geometry 3D model type, the voxelization method assigns each primitive composing the object a unique bit location in a color value. The frame buffer hardware pixel map is then used to classify the voxels within the slice as either inside or outside each primitive based on the color value associated with that voxel. The frame buffer hardware pixel map is used to classify the voxels within the slice as either inside or outside the object based on the classification of the voxels as either inside or outside each primitive.

In accordance with another aspect of the present invention, the method for voxelizing an object is used to voxelize a generalized CSG model of an object in 3D space by first converting the generalized CSG model into a binary volume representation of the object, then voxelizing this binary volume. The 3D space includes a plurality of coordinate points. The object is composed of a plurality of primitives. The generalized CSG model includes a generalized CSG tree having a lowest level consisting of a child node associated with each primitive of the object, at least one binary node associated with two child nodes at a level below. Each binary node includes an associated Boolean operation that governs the interaction between its associated child nodes. Each child node is associated with only a single binary node above. A leaf node is formed by the binary node at the highest level of the CSG tree and composed of two child nodes below. Each binary node other than the leaf node forms a child node for a binary node above. The step of converting to the volume model involves for each point in 3D space, creating a classification index for the point indicative of whether the point is interior to or exterior to each primitive. Next, for each primitive, a point classification map is created that maps each classification index against the primitive and its associated child node of the CSG tree. Then for each child node, a point classification map is determined for its associated binary node based on the child node's point classification map, the point classification map of the other child node associated with its binary node, and the Boolean operation associated with the binary node. Next, for each binary node, a point classification map is determined for its associated binary node above based, on the binary node's point classification map, the point classification map of the other node associated with the binary node above, and the Boolean operation associated with the binary node above. The point classification maps are recursively determined for binary modes until the point classification map is determined for the leaf node, thereby creating the binary volume model of the object. This binary volume model is then voxelized.

According to another aspect of the current invention, the step of creating a point classification map for each coordinate point includes the step of assigning an n-bit word to each point, where "n" is the number of primitives comprising the object. Each primitive is associated with a unique one of the bits of the n-bit word. The value in each bit represents whether or not the particular primitive contains the particular point to which the n-bit word is assigned.

Further embodiments, features and advantages of the present invention, as well as the structure and operation of the various embodiments of the present invention, are described in detail below with reference to the accompanying drawings.

BRIEF DESCRIPTION OF THE DRAWINGS

The accompanying drawings, which are incorporated here and form a part of the specification, illustrate the present invention and, together with the description, further serve to explain the principles of the invention and to enable a person skilled in the pertinent art to make and use the invention.

In the drawings:

FIG. 10 is a flow chart of the pseudocode used to implement the present invention for objects in curve/surface 3D space.

FIG. 11 is a flow chart of the pseudocode used to implement the present invention for objects in solid boundary representation 3D space.

FIG. 13 is a table showing the color status of the pixels associated with the voxels of FIG. 14.

FIG. 23 is a flow chart of the pseudocode used to implement the present invention for objects in VCSG 3D space that are first converted to binary volume representations.

FIG. 24 is a flow chart of the pseudocode used to implement one particular module of the pseudocode of FIG. 23.

FIG. 26 is a diagram of a chart that describes certain relationships underlying the pseudocode of FIG. 24.

The present invention will now be described with reference to the accompanying drawings. In the drawings, like reference numbers indicate identical or functionally similar elements.

DETAILED DESCRIPTIONS OF THE PREFERRED EMBODIMENTS

Figure 3:
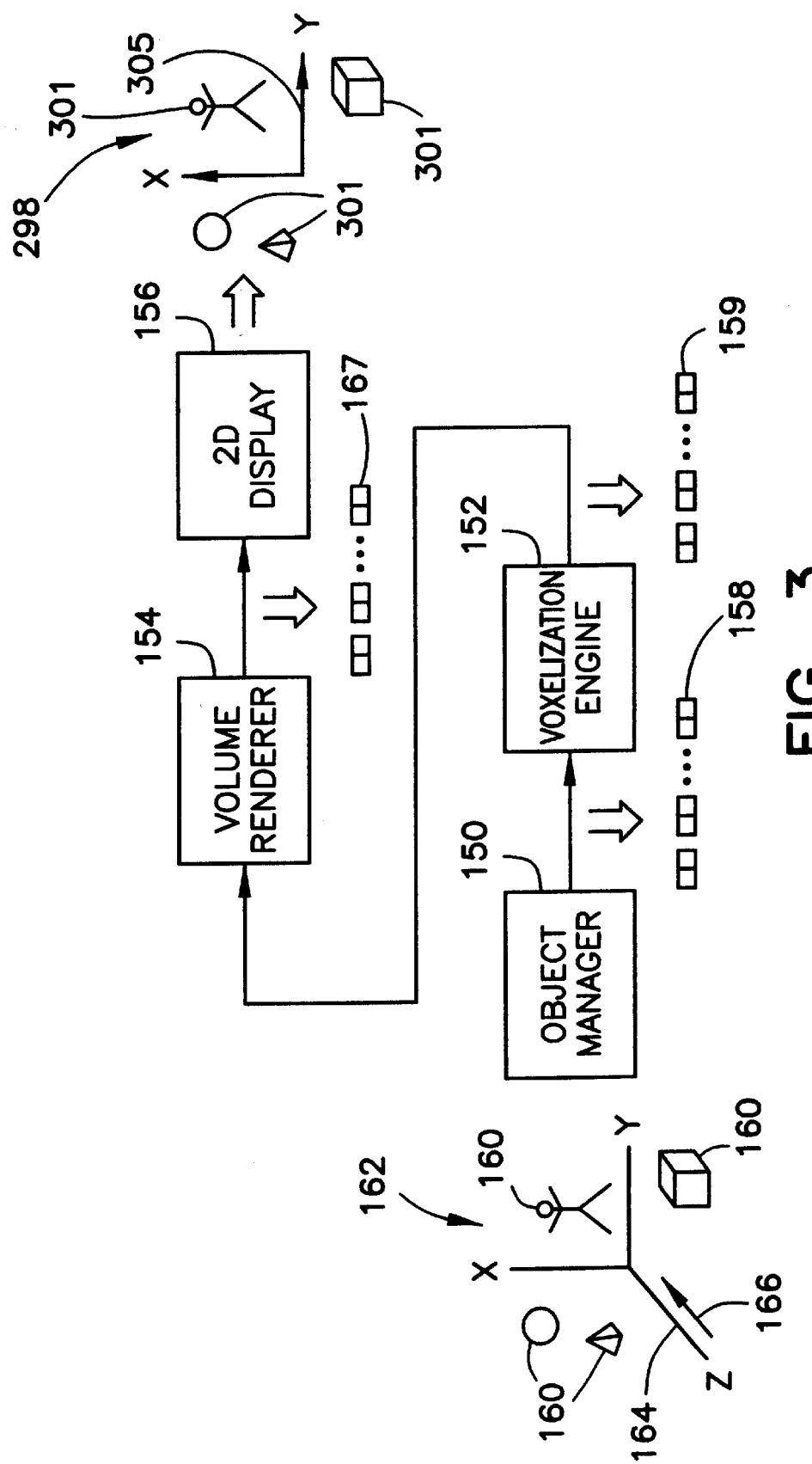
FIG. 3 is a block diagram of the stages of the method of the present invention implemented on the computer system of FIG. 1A using the software of FIG. 2.

I. Overview and Discussion
II. Computer Graphics System
III. Overview of Computer System Software Components
IV. Object Manager
V. Voxelization and Volume Rendering
   A. Curve/Surface Model
   B. Solid Voxel (Boundary/Surface) Model
   C. VCSG Model
      1. Scalar Approach
      2. Binary Approach (When Voxelizing, treat all 3D objects as solids)
VI. 2D Display
VII. Alternatives to Volume Rendering and 2D Display I. Overview and Discussion In such diverse applications as CAD/CAM and medical imaging/diagnostics, 3D models of 3D objects are manipulated in their 3D environments. Often one application will require interaction, manipulation and display of both volume and geometric 3D models. As shown in FIG. 3, the method of the present invention handles mixed 3D models by first voxelizing each 3D object using a voxelization technique appropriate to its particular 3D model type. Then the voxelized models are uniformly processed (e.g. displayed) using volume graphics techniques (e.g. volume rendering). Even using this relatively fast method, the step of voxelizing the 3D models is relatively computationally intense. As such, voxelization typically cannot be adequately performed in real time using current techniques with current hardware and software systems.

Using existing hardware and software systems, however, one embodiment of the present invention provides an apparatus and method for rapidly voxelizing 3D models of 3D objects. In particular, new uses are made of certain existing graphics commands of a graphics API and any associated hardware that implements these commands (the "Dual Use Technology"). This Dual Use Technology was originally designed and intended to perform graphics operations, such as texture mapping and color blending, on 2D and 3D objects. As described further below, the Dual Use Technology includes hardware such as logic engine 101, Texture Memory 109 and Frame Buffer Memory 107 (depicted in FIG. 1B) and the frame buffer blending commands of 3D Graphics API 208 (shown in FIG. 2).

As an added benefit of the first embodiment of the present invention, in some cases voxelization using the Dual Use Technology leaves the Texture Memory 109 and/or the Frame Buffer Memory 107 substantially in its initial state for volume rendering. Since volume rendering is the next step in displaying a 3D object in 2D, this embodiment saves time volume rendering.

A second embodiment of the present invention redesigns existing hardware and software with relatively minimal changes to optimize the voxelization method of the present invention. This second embodiment is described together with the description of the first embodiment by highlighting any necessary or preferred changes to existing hardware and associated software.

II. Overview of Computer Hardware Components

Figure 1A:
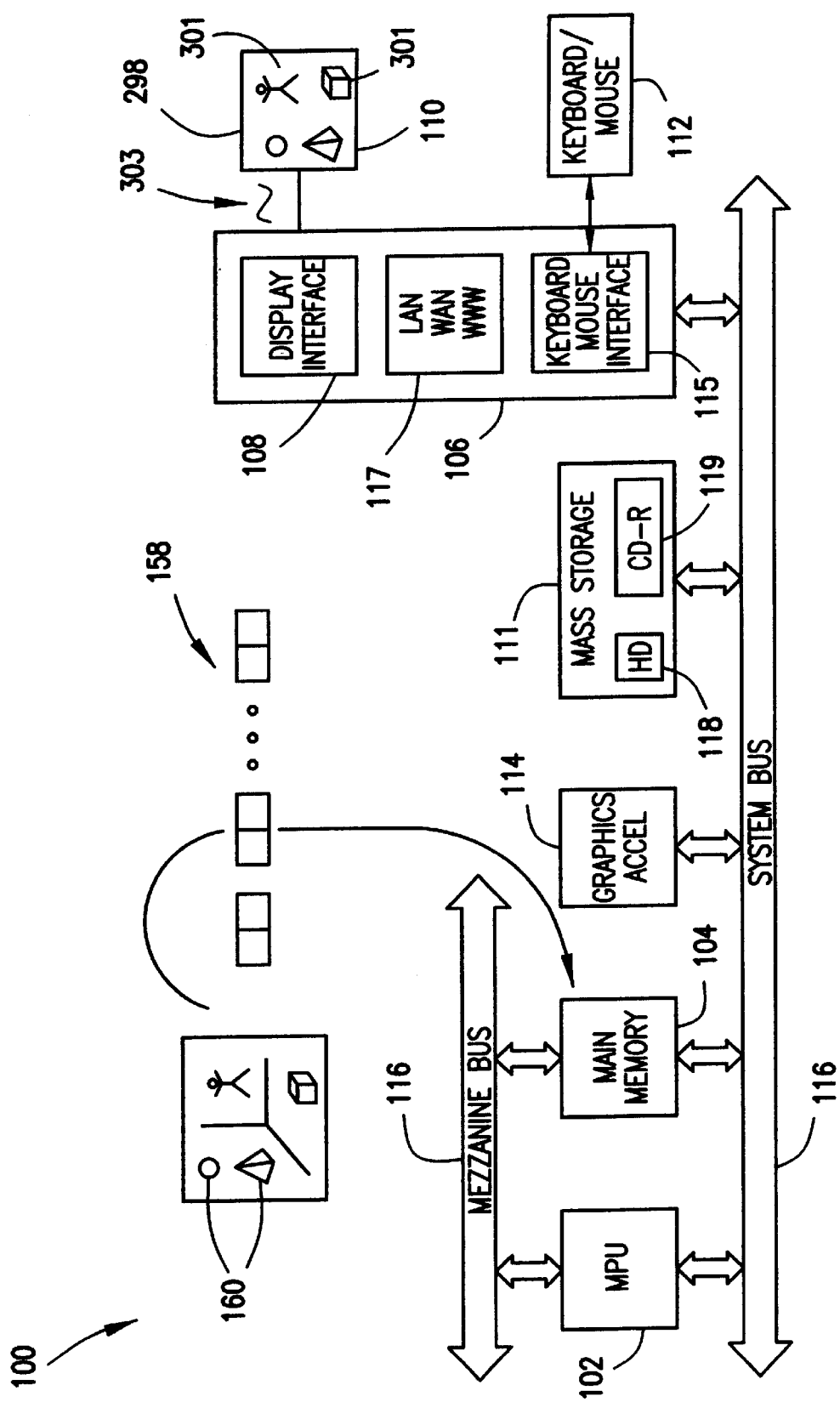
FIG. 1A is a block diagram illustrating a preferred computer system for implementing the present invention.
Figure 5B:
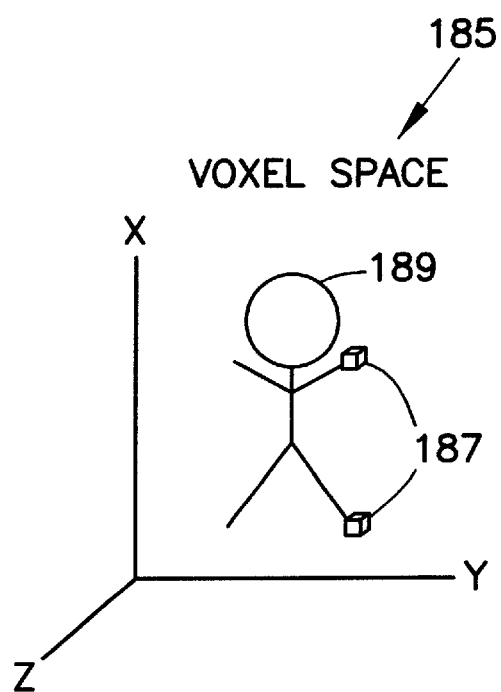
FIGS. 5A–B show schematic diagrams illustrating the voxelization of a continuous 3D solid object represented by boundary surfaces in 3D object space into a discrete 3D volumetric object represented in 3D voxel space, according to the principles of the present invention.
Figure 5A:
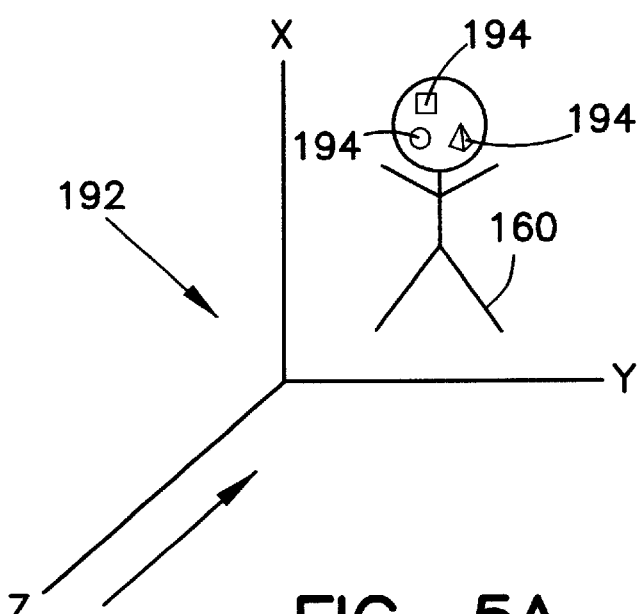
Figure 6B:
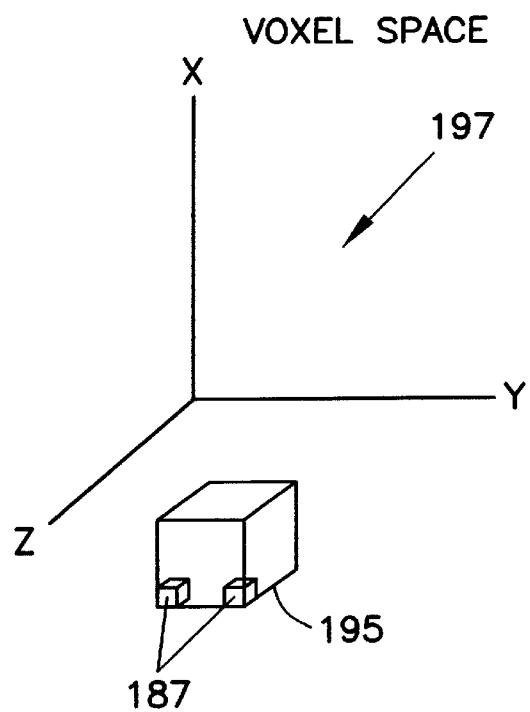
FIGS. 6A–B show schematic diagrams illustrating the voxelization of a volumetric CSG model in 3D space into a discrete 3D volumetric object represented in 3D voxel space, according to the principles of the present invention.
Figure 6A:
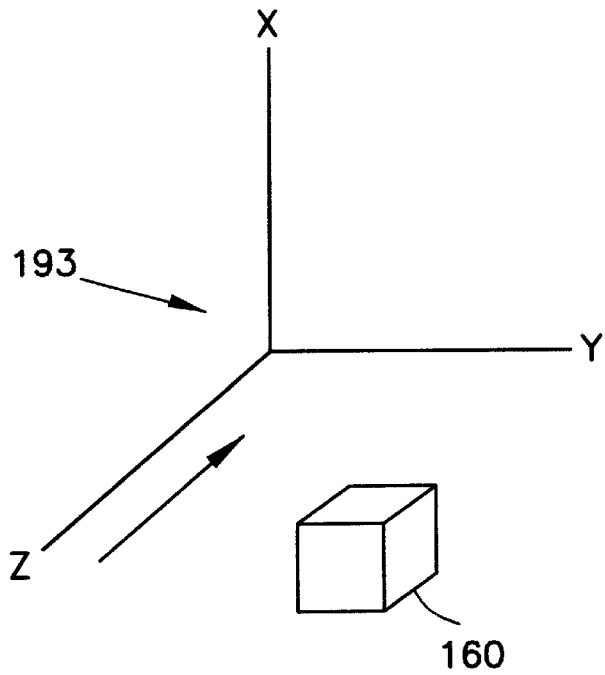
Figure 7:
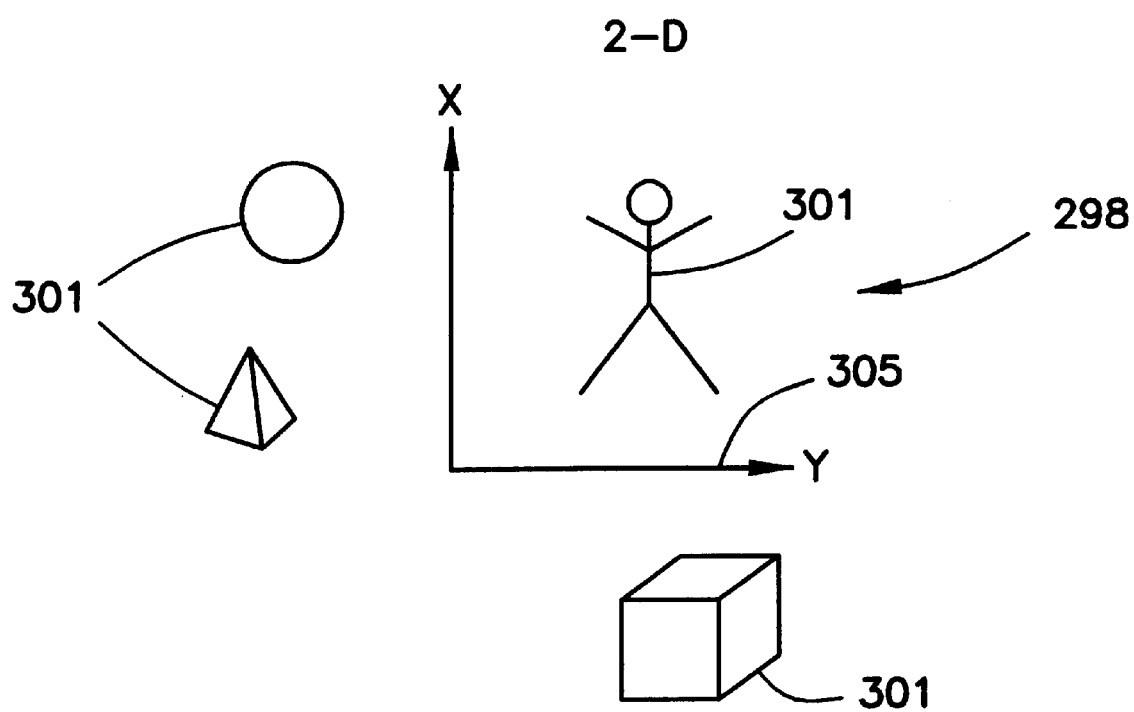
FIG. 7 is a pictorial representation of the objects in FIGS. 3, 4A–B and 5A–B displayed in 2D on a display monitor of the computer system in FIG. 1A, after the objects have been voxelized and then rendered according to the principles of the present invention.

Referring now to FIGS. 1A, 1B, 2, 3, 4A, 5A, 5B, 6A, 6B, 7 and 8, in FIG. 1A there is shown a broad block diagram illustrating a preferred computer system 100 for implementing embodiments of the present invention. For the first preferred embodiment of the present invention, computer system 100 is of a type commercially available today, with only "off the shelf" hardware and software 200 (except for the software 217 in FIG. 2 that implements the current invention). Computer system 100 is loaded with and runs software 200 (shown in FIG. 2) that, among other things, implements the method of the present invention to manipulate 3D objects 160 (shown in FIGS. 1A, 3, 4A, 5A, and 6A) and convert them into 2D object representations 301 suitable for display in 2D space 298 (as shown in FIGS. 3 and 7).

Figure 8:
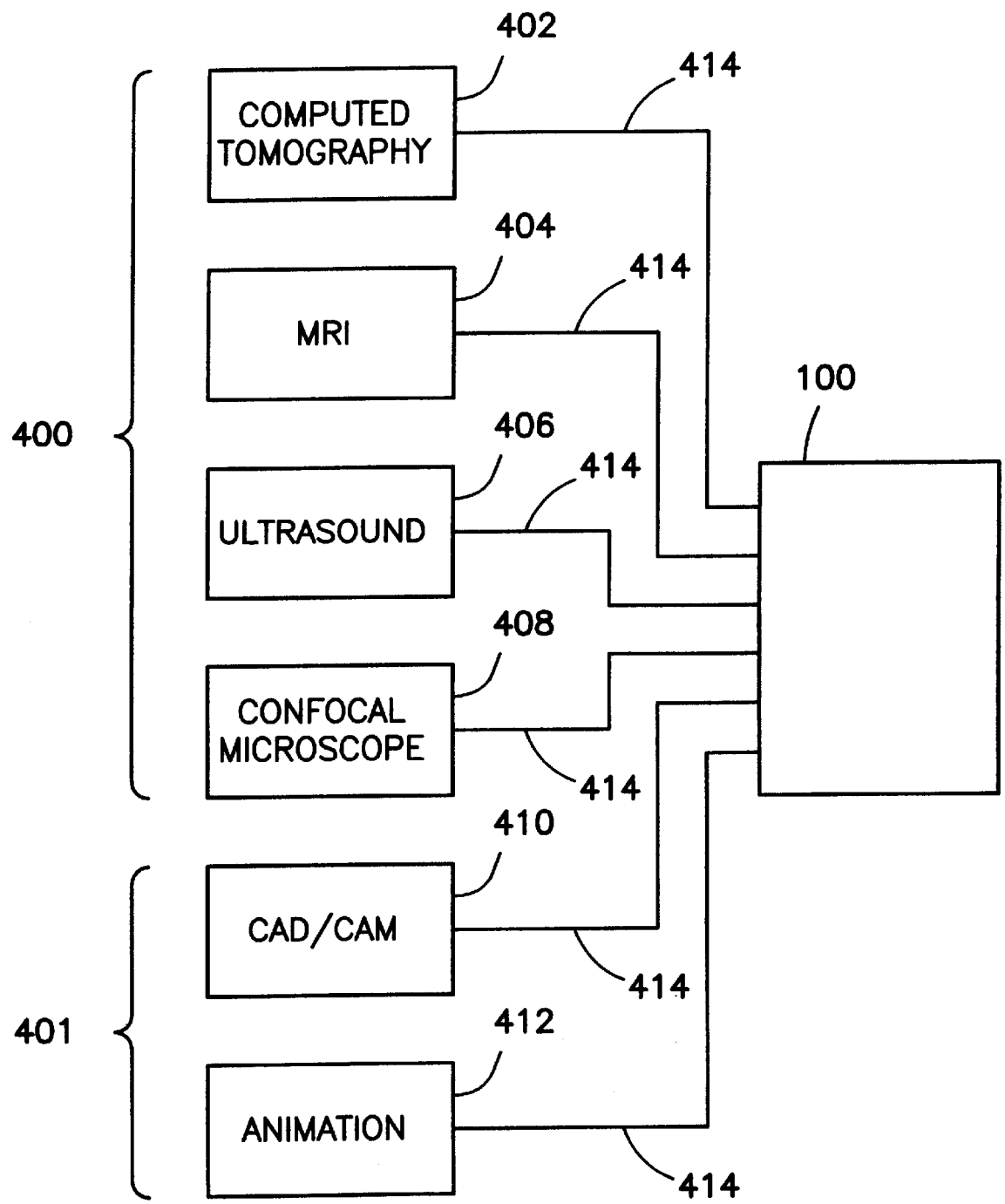
FIG. 8 is a block diagram showing possible sources of the 3D objects manipulated by computer system 100 of FIG. 1A.

Typical sources of 3D objects 160 include various medical imaging equipment 400, such as Computed Tomography (CT) 402, MRI 404, ultrasound 406 or confocal microscope 408 and various computer modeling equipment 401, such as CAD/CAM system 410 and computer animation system 412 (shown in FIG. 8). These devices 400 and 401 typically are connected to computer system 100 via a communication channel 414, such as dedicated cable (fiber or wire), wireless link (RF or IR), the Intranet, or an intranet such as a Wide Area Network (WAN) or a Local Area Network (LAN).

As shown in FIG. 1A, computer system 100 includes one or more microprocessor units 102, each including one or more microprocessor units (MPU) 102 (each one consisting of a central processing unit or CPU, associated cache memory, memory management units and other components well known to those skilled in the relevant art (not shown)). Computer system 100 further includes mass storage 111, such as hard drive 118 and/or re-writeable CD drive 119, main memory 104, Input/Output Subsystem 106, graphics accelerator 114 and one or more buses 116 that allow one or more of these and other components to exchange control and/or data signals. Computer system 100 further includes display monitor 110 and keyboard/mouse 112.

Preferably computer system 100 is an Onyx-2 (TM) workstation made by Silicon Graphics, Inc., using a single processor Reality Engine (TM) and 64 MB of texture memory 105. However, other suitable computer systems 100 include an Intel Pentium (TM)-based personal computer with appropriate graphics accelerator 114, or similar systems.

Graphics accelerator 114 preferably includes specialized hardware and associated firmware to accelerate 2D and 3D graphics operations, such as blending and texture mapping. In particular, graphics accelerator 114 includes logic engine 101, Z or depth buffer 97, frame buffer 99 and texture map 105. Logic engine 101 is operationally connected to buffers 97 and 99 and texture map 105. Engine 101 consists of specialized hardware and firmware (not shown) that performs graphics operations (such as blending and texture mapping) more rapidly than such operations could be performed in software 200 in MPU 102. Alternatively, these logic operations can be performed, via software, by MPU 102.

Depth buffer 97 is a memory structure that maintains in memory 94 the identity of the object 160 (shown in FIG. 3) that, when rendered, appears as the object representations 301 "closest" to front of the display screen of display monitor 110. Frame buffer 99 is a memory structure that maintains in memory 107 a two-dimensional array (typically in Cartesian coordinates, x–y) of pixels 95. This two-dimensional array is a "frame" of pixels 95 that will be displayed as 2D object representations 301 on display monitor 110 via I/O subsystem 106. Preferably, frame buffer 99 includes its own, dedicated, relatively fast memory 107 on graphics accelerator 114. Alternatively, frame buffer 99 can reside in portion (not shown) of main memory 104 or in memory (not shown) in display interface 108 in I/O subsystem 106.

Figure 1B:
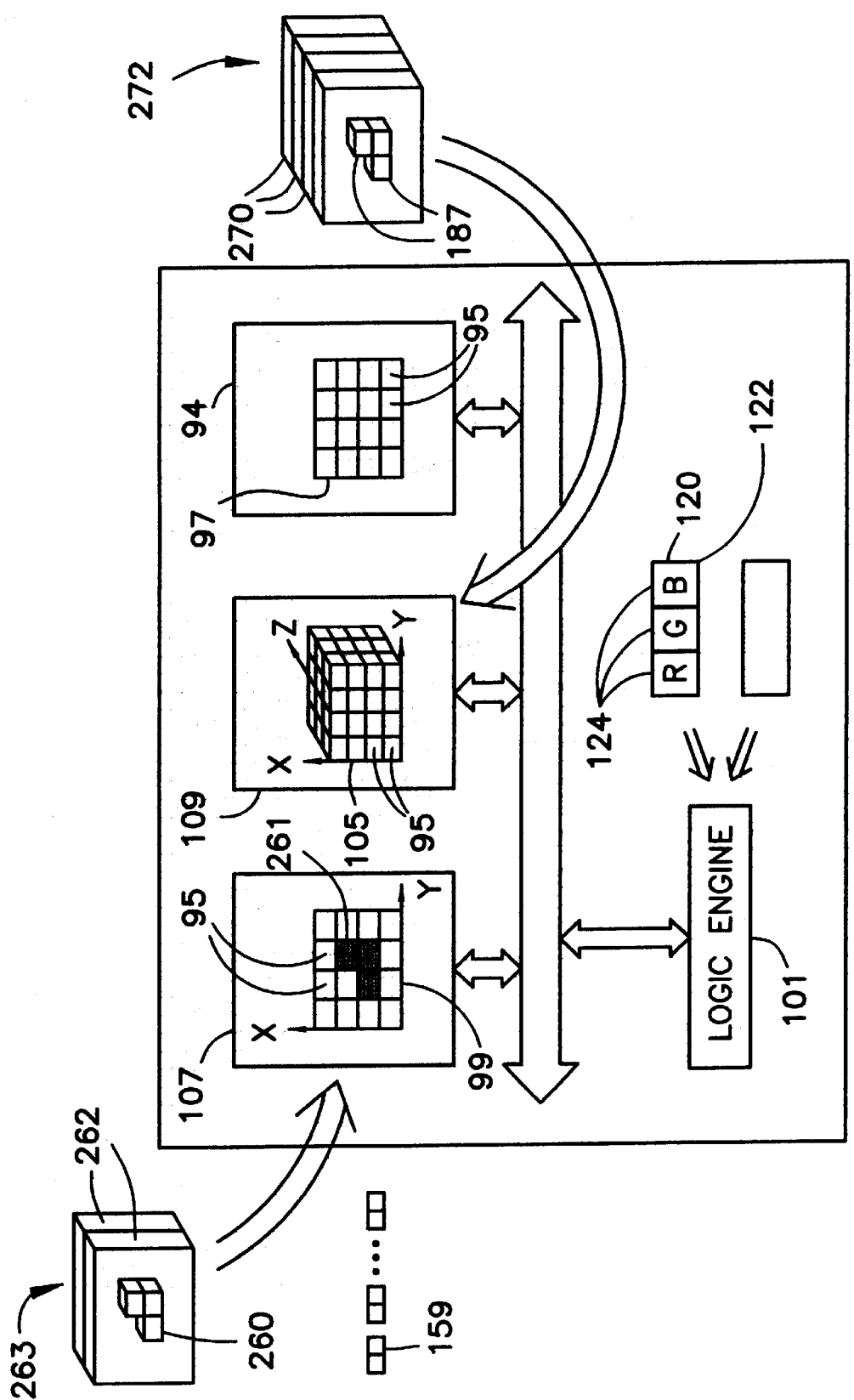
FIG. 1B is a schematic diagram illustrating the components of the graphics accelerator of FIG. 1A and their interaction of implement the present invention.

Preferably, graphics accelerator 114 further includes a texture map memory structure 105, stored in special texture mapping memory 109, for holding data on which texture mapping is being performed by logic engine 101. Preferably memory 109 is configured in a 3D matrix for storing 3D representations both prior to and after texturing of such representations. Preferably, this memory 109 is relatively fast random access memory (RAM). In FIG. 1B, texture memory 109 is shown as a component of graphics accelerator 114. Alternatively, this memory 109 can be a portion (not shown) of main memory 104. Preferably, texture map 105 is a 3D structure, implemented in Cartesian coordinates. Alternatively, map 105 can be a 2D structure, with any required 3D operations implemented reading and writing from and to, respectively, other memory, such as main memory 104.

I/O Subsystem 106 includes LAN/WAN/Internet interface 117 (such as a cable modem, phone modem, fast Ethernet (TM), DTH satellite downlink or other communication connection), keyboard and mouse interface 115 for connecting to keyboard/mouse device 112, and monitor interface 108 for connecting to display monitor 110.

In operation, data 158 representing 3D graphical objects, such as objects 160, resides in either mass storage 111 or main memory 104 prior to computer system 100 using the method of the present invention to voxelize and then volume render the objects to generate corresponding 2D images 301 on display monitor 110.

III. Overview of Computer System Software Components and Associated Computer Hardware Referring now to FIGS. 1A, 1B, 2 and 3, in FIG. 2 there is shown a pictorial representation of the system software 200 included in computer system 100. In FIG. 3 there is shown a block diagram of the stages of the method of the present invention implemented on the computer system of FIG. 1A using the system software 200. System software 200 includes an operating system 202 (such as Windows NT, Linux or Unix, DOS, CP/M, Solaris or other operating system well known to one skilled in the art), firmware 203 that controls the operation of computer system 100 at a lower level than operating system 200 (e.g., BIOS) and various device drivers 204 for driving devices such as display monitor 110 and keyboard/mouse 112. System software 200 also includes specialized graphics commands 206 (e.g., BTBLT) recognized by certain hardware components of computer system 100 that provide for more rapid execution of certain graphics operations. Software 200 further includes a Graphics Applications Programming Interface (API) 208 that allows programmers to more readily generate applications that take advantage of specialized graphics commands 206.

System software 200 also includes software 217 that implements the preferred embodiments of the method of the present invention. Software 217 includes four components that correspond to the four stages of the system block diagram 148, shown in FIG. 3. Software 217 includes object manager application 210, voxelization application 212, volume rendering application 214 and 2D display application 216, which implement, respectively, the stages of object manager 150, voxelization engine 152, volume renderer 154 and display 156.

In brief, the stage of object manager 150 (and the associated object manager application 210) allow an operator or interactive software application (such as CAD/CAM 230) to manipulate various 3D objects 160 in one or more congruent 3D object spaces 162, represented in FIG. 3 for simplicity by the same Cartesian coordinate system 164. Objects 160 may be of the same or different 3D model (e.g., objects 160 can be both synthetic and based on "real" data, say from MRI device 404 in FIG. 8).

Manipulations to an object 160 include rotating, translating or changing one of the object's 160 other properties, such as the color or transparency of the object 160 or certain portions of object 160. Manipulations of the objects 160 may change the relationship of the objects 160 with respect to each other, for example by causing one object 160 to occlude another object 160 from the perspective of viewing direction 166, or even causing an object 160 to intersect another object 160. Once objects 160 have been manipulated, data 158 representing each object is passed to voxelization engine 152 (and the associated voxelization application 212).

Note, however, that preferably each time an object 160 is manipulated, the object 160 must be "re-voxelized." That is, object manager stage 150 manipulates objects 160 in their native 3D spaces. This is done so that manipulations of objects 160 take place in their "native" application (such as CAD/CAM 230).

Figure 4B:
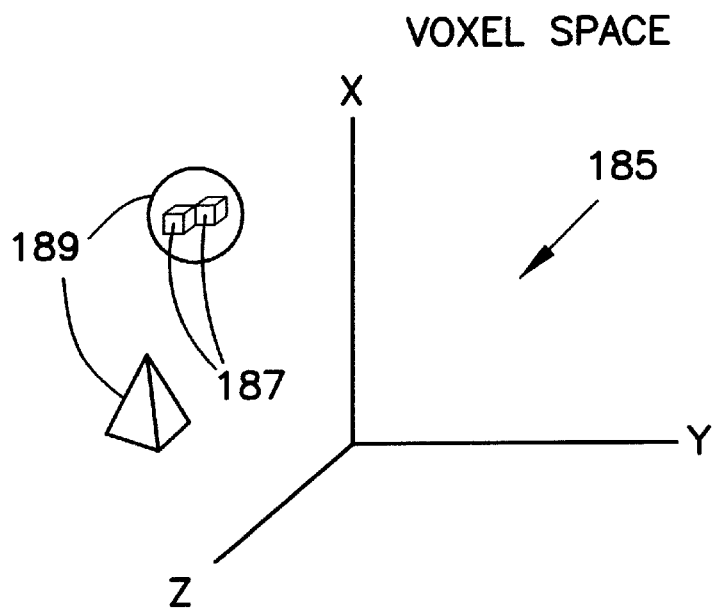
FIGS. 4A–B show schematic diagrams illustrating the voxelization of a continuous 3D object represented in continuous 3D geometrical object space into a discrete 3D volumetric object represented in 3D voxel space, according to the principles of the present invention.

In the voxelization engine stage 152, data 158 representing objects 160 are manipulated to transform each object 160 from its native 3D model (or models, in the case of a 3D object composed of primitives of more than one 3D model type) to data 159 representing objects 189 in voxel space 185 (as shown in FIGS. 4B and 5B, or to data 159 representing object 195 in voxel space 185 as shown in FIG. 6B. Typically each type of 3D model requires a different voxelization technique. In accordance with the method of the present invention, voxelization software 212 includes a specialized algorithm (algorithms 300, 310, 330, 730, and 732, in respective FIGS. 10, 11, 17, 23, and 24) for each type of 3D model that rapidly voxelizes the objects 160 of that model type.

How each type of 3D model is identified is well known to one skilled in the art, and so will not be discussed here. Typically, however, data 159 is organized according to a protocol that includes overhead data (not shown) which identifies the type of 3D model.

As discussed further below in Section V. Voxelization and Volume Rendering, in the first preferred embodiment these algorithms work in part by using certain commands of the 3D Graphics API 208 and certain components of the graphics accelerator 114 in manners not intended by their designers. In the second preferred embodiment, minor changes would be made to API 208 and the components of graphics accelerator 114 to optimize these algorithms.

Once an object 160 or group of objects 160 has been voxelized, data 159 representing the voxelized objects 189 are passed to volume rendering stage 154. Volume rendering stage 154 converts the volume representation of each object 189 into a 2D representation 301 in 2D space 298, a process known as "volume rendering." As discussed further below in Section V. Voxelization and Volume Rendering, at the start of the volume rendering process, preferably the voxelization engine stage 152 has placed data 159 in texture memory 105 in a form suitable for direct application of a standard volume rendering technique.

After volume rendering, data 167 representing the volume rendered objects are passed to the 2D display stage 156 and preferably placed in frame buffer 99. Display stage 156 converts data 167 into a form suitable for displaying object representations 301 in 2D 298. For example, as shown in FIG. 1, in stage 156 display interface 108 can produce signals 303 which display object representations 301 on display monitor 110.

IV. Object Manager

Figure 2:
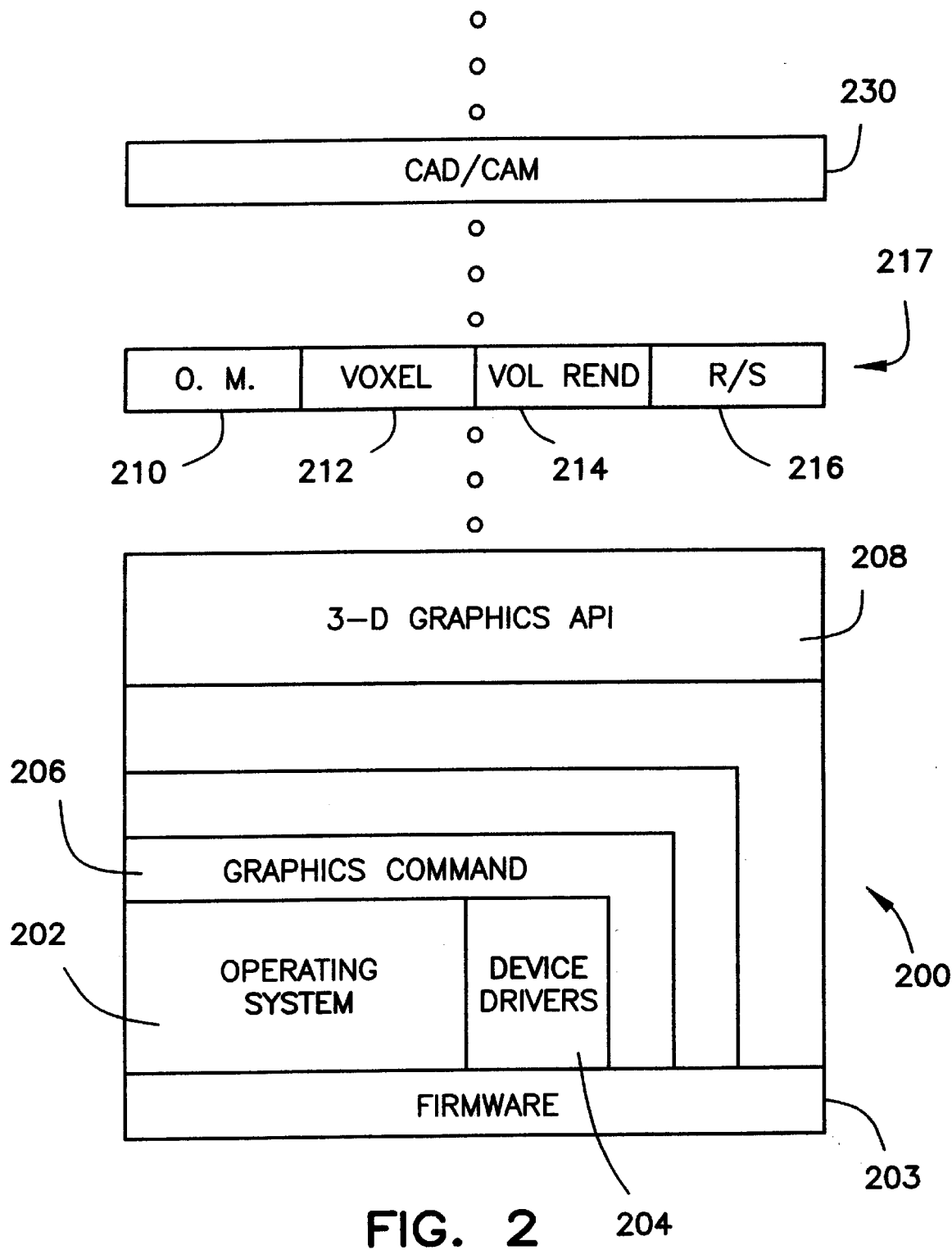
FIG. 2 is a pictorial representation of the various software applications of the computer system of FIG. 1A, configured in accordance with the principles of the invention.

Referring now to FIGS. 2 and 3, the task of the object manager 150 is to manage the interactions among objects 160 in their native 3D space. For example, if an object 160 has been created by CAD/CAM application 230, then object manager application 210 (the software application that implements object manager 150) calls upon CAD/CAM application 230 for any needed manipulation of object 160.

V. Voxelization and Volume Rendering

In brief, referring now to FIGS. 1A, 1B, 2, 3 and 9, voxelization engine stage 152 processes objects 160 by first generating slices 180 of the objects 160, and then for volume reconstruction writing the data 159 representing each slice 180 to frame buffer 99. In this manner, the pixels 95 of frame buffer 99 actually contain data representing voxels 260.

Frame buffer 99 is a memory structure typically maintained by graphics accelerator 114. Frame buffer 99 preferably is implemented in relatively fast frame buffer memory 107. Buffer memory 107 can be dedicated memory (as shown in FIG. 1B) or could be one "z" plane of texture memory 109, with frame buffer 99 actually one "z" plane of texture map 105. Alternatively, frame buffer 99 can reside in relatively slower main memory 104, with slower performance as a consequence.

In the first preferred embodiment of the voxelization method and apparatus of the present invention, extensive use is made of existing hardware of computer system 100. For example, during the process of slice generation, frame buffer blending functions (not shown) are used by logic engine 101 to carry out the necessary voxelization computations in relatively fast hardware. When the data 159 from the voxelization stage 152 is written into a frame buffer 99 residing in one "z" plane of texture map 105 of texture memory 109, volume rendering stage 154 can immediately and interactively perform volume rendering using the 3D texture mapping function of logic engine 101 and associated graphics commands 206 and graphics API 208. When the data 159 is written into a frame buffer 99 residing in separate frame buffer memory 107, data 159 must first be written into texture map 105 for volume rendering state to perform such volume rendering.

Although the above approach is used for many types of 3D models, the details of the approach vary depending on the particular 3D model. The implementation details for the voxelization stage 152 for the three most common types of 3D models, curve/surface, solid voxel (a/k/a boundary solid representation) and VCSG, are given below, followed by the associated volume rendering stage 154. The 2D Display stage 156 is rather straightforward and will be treated separately later.

V.A. Curve/Surface Model

Figure 4A:
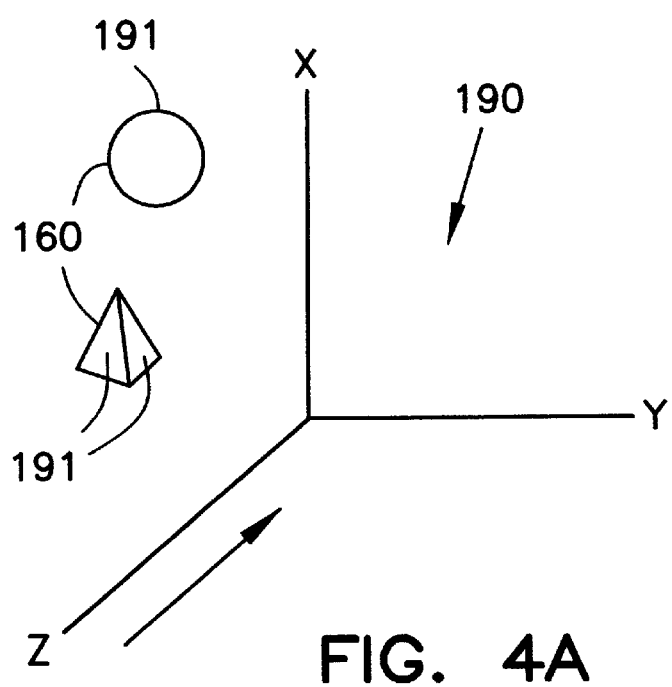

Referring now to FIGS. 1A, 1B, 2, 3, 4A, 4B, 9 and 10, in FIG. 10 there is shown the pseudocode algorithm 300 used in the voxelization engine stage 152 by voxelization software 212 to voxelize objects 160 (shown in FIGS. 1A and 4A) constructed using the curve/surface 3D model. (The pseudocode used in this and other figures is, essentially, a computer language using universal computer language conventions. While the pseudocode employed here has been invented solely for the purposes of this description, it is designed to be easily understandable by any computer programmer skilled in the art.) Referring now to FIGS. 4A and 4B, objects 160 are part of a 3D space 190 that represents objects 160 as an arbitrary number of curve or surface objects 191 (e.g., lines, polygons, quadratic surfaces and curves, and Non-Uniform Rational B-Splines (CURBS) curves and surfaces). After voxelization, objects 160 have been converted to volume or voxel objects 189, composed of voxels 187, in voxel space 185.

The basis of algorithm 300 is the observation that such objects 160 in curve/surface 3D space 190 are displayed by a 2D display process (e.g., onto a computer monitor 110 shown in FIG. 1A). When only a slice 180 of an object 160 is displayed, the result is essentially a slice of the volume from a 3D scan conversion. Algorithm 300 takes advantage of 2D scan conversion being implemented in hardware, such as by graphics accelerator 114 and associated memory 104, 105 and 107.

Referring now to FIGS. 1A, 1B, 9 and 10, in algorithm 300, the first step 302 is to initialize the display environment. This includes creating an appropriately sized bounding box 240 to encompass the relevant objects 160 in 3D space 190, defining the desired lighting and texturing for each object 160 and enabling polygon anti-aliasing and line anti-aliasing (if available in computer software 200 and/or graphics accelerator 114). Box 240 defines the portion of space 190 for voxelization. For simplicity, box 240 can be a cube of dimensions N×N×N pixels. Of course, however, other dimensions may be used provided suitable accommodations are made for handling the resulting data and memory structures, as would be well known to one skilled in the art.

Next, in step 304 the parameters are set for using slice 180 to slice the objects 160 in bounding box 240. Each slice 180 is formed as the space between two adjacent (i.e., separated by one pixel) Z-planes 242 and 244 within the box 240. Preferably Z-planes 242 and 244 are oriented substantially perpendicular to viewing direction 274 to reduce the need at a later stage in the display of the 2D object for further calculations or manipulations to generate the image from the perspective of viewing direction 274.

The first z-plane 242 is the front face 246 of the bounding box 240. The last z-plane 244 is the back face 248 of bounding box 240 (i.e., the face further from the hypothetical viewer along axis 274). The four side "walls" 252 of slice 180 are each formed between the intersection of a plane 242 or 244 with the y-axis and x-axis boundaries of bounding box 240. Note that the resolution of the voxelization process is dependent on the relative dimensions of a pixel in each of the three axes.

Figure 9:
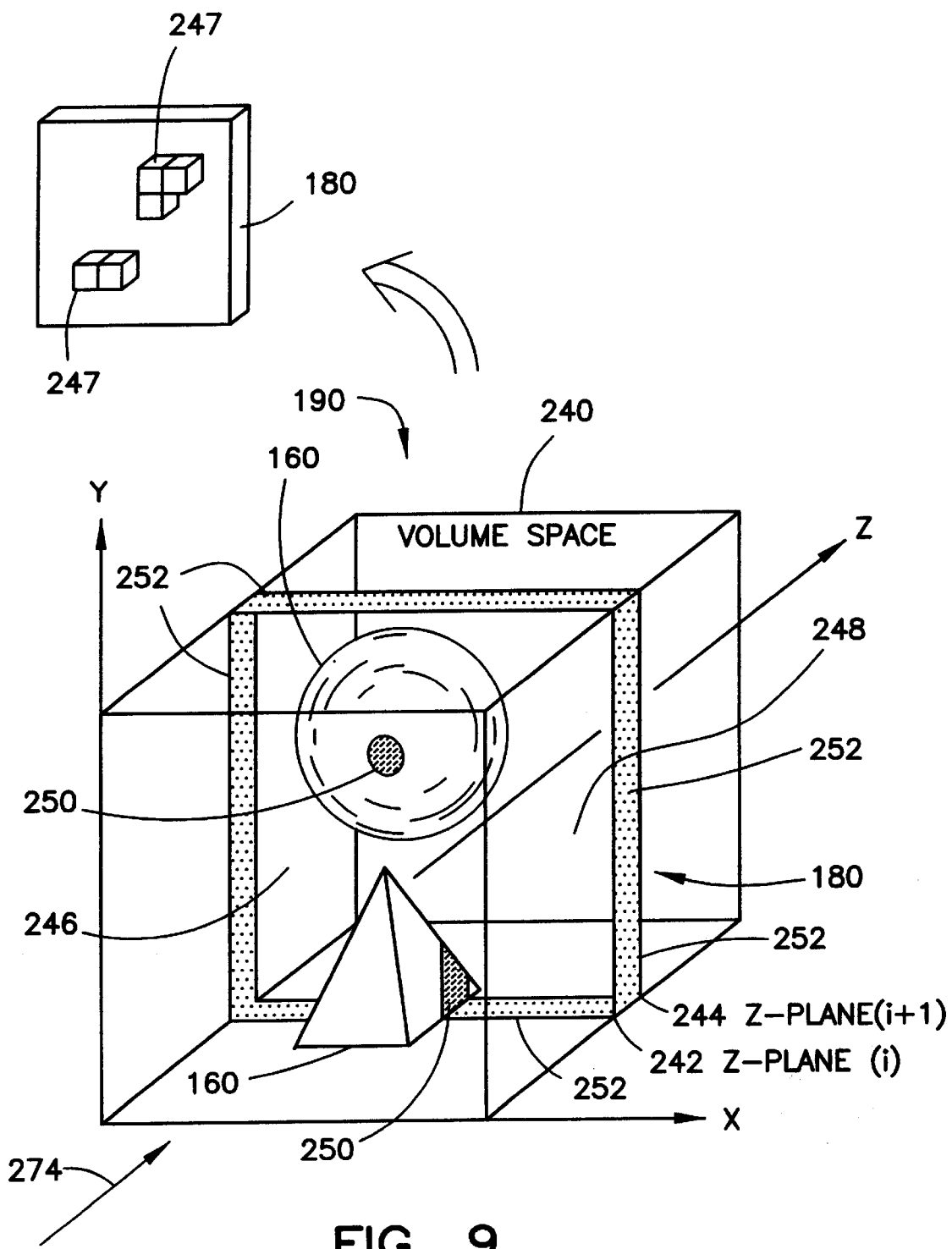
FIG. 9 is a pictorial representation of an object in curve/surface 3D space and certain aspects of the voxelization of the object in accordance with the principles of the invention.

In step 306 a slicing loop is performed, moving the slice 180 in sequence from the front face 246 to back face 248 of the bounding box 240. For each slice 180, step 306 renders all the curve and surface primitives 250. Preferably software 200 (shown in FIG. 2) includes as its 3D graphics API 208 the OpenGL (TM) API to perform this rendering (Version 1.2). OpenGL is a hardware-independent Application Programming Interface (API) 208 that provides an interface to graphics operations. Since in OpenGL, the boundary planes 242 and 244 and four walls 252 that form slice 180 are considered clipping planes. As shown in FIG. 9, the clipping mechanism (not shown) of graphics accelerator 114 will ensure that only the surface fragments 247 of the curves or surfaces of objects 160 within slice 180 are displayed.

Preferably, the data 159 (shown in FIGS. 1B and 3) generated by OpenGL API 208 and associated with each particular slice 180 are stored as they are created in frame buffer 99 (shown in FIG. 1B). The resulting frame buffer 99 image 261 (shown in FIG. 1B) becomes one "slice" 262 of the voxelization result of the 3D space 190.

With the stepping of slices 180 from front face 246 to back face 248, algorithm 300 basically generates the slices 262 of the volume representation 263 in a front-to-back order. Preferably, each such slice 262, once generated in frame buffer 99, is written to 3D texture map 105 as one slice 270 of a texture volume 272. In this manner, texture volume 272 can then be immediately rendered (stage 154) by 3D texture mapping (a technique well known to those skilled in the art), as implemented in logic engine 101 in graphics accelerator 114.

Alternately, all slices 270 of texture volume 272 can be accumulated in texture map 105 in texture memory 109, then written directly to main memory 104.

When texture mapping is not available in graphics accelerator 114, each slice 262 of volume representation 263 can be written directly from the frame buffer 99 to main memory 104 rather than to texture map 105 in texture memory 109. Note, however, that typically writing the frame buffer 99 to the texture map 105 in memory 109 is a much faster operation than writing buffer 99 to main memory 104, particularly if the frame buffer 99 is stored in special frame buffer memory 107 (as shown) rather than in main memory 104. Thus, if texture memory 109 is available, the volume 272 produced by algorithm 300 should be rendered and examined in 3D texture memory 109 before being written to main memory 104.

Note that 3D texture mapping is not required for curve/surface voxelization. On computer systems 100 with only 2D texture mapping supported by graphics accelerator 114, data 159 representing slices 270 can be stored in 2D texture memory 105 (or in main memory 104) as separate 2D textures rather than as 3D textures. Then, in the rendering stage 154, use can be made of a Shear-Warp projection process described in "Shear-warp volume rendering by 2D texture mapping, a technical report by Shiaofen Fang and Yi Dai, Department of Computer and Information Science, Indiana University Purdue University Indianapolis, 1999, and incorporated herein by reference), which is similar to the raycasting-based Shear-Warp algorithm described in "Fast volume rendering using a shear-warp factorization of the viewing transformation," by P. Lacroute and M. Levoy, in SIGGRAPH '94, pages 451–458, 1994. In this manner, the curve/surface voxelization algorithm 300 can be used by personal computers 100 with only 2D texture mapping support.

Referring now to FIGS. 1A, 1B, 9 and 10, it is preferable to have anti-aliasing enabled in all relevant stages 152, 154 and 156 (e.g., in step 302 by enabling the anti-aliasing features in the OpenGL API 208). Without anti-aliasing enabled, in step 304 when a polygon or a line (not shown) has a small angle with respect to the viewing direction 274 (the Z axis), the voxels 187 generated for this polygon may not form a connected surface or curve in volume or voxel space 185. Even if the resulting surface is connected, it may not be thick enough to satisfy the tunnel-free requirement. When such a representation is 2D scan-converted in stage 156, the limited sampling resolution in 2D scan conversion stage 156, coupled with fragmentation of the objects 160 from the voxelization stage 152 may result in an inadequate display of object representations 301 on monitor 110.

Although the implementations of anti-aliasing can be different in different computer systems 100, graphics APIs 208 and graphics accelerators 114, the principle is always to assign a pixel color proportional to the area of the pixel covered by the line (with a thickness) or a polygon (not shown). This essentially colors all voxels 187 that have intersections with an object 160 in the volume 270, which apparently satisfies the connectivity and tunnel-free requirements. The anti-aliasing result, however, may not necessarily be minimal (i.e., the voxels 187 may not be the minimal set necessary to describe the curve or surface). But minimality is not always necessary and desirable. The extra boundary voxels 187 generated from anti-aliasing provide the necessary smoothing for the rendering of the volume representation in stage 154.

An important feature of algorithm 300 is that many surface graphics rendering effects (not shown) can be easily carried over to the volume representation 272. This is due to the actual pixel colors from the curve/surface rendering being directly copied to texture volume 272. Thus, many rendering effects, such as shading and surface texturing enabled for the surface display of the slices 180, are automatically stored in the texture volume representation 272. These can be rendered later in stage 154 without extra computation by computer system 100.

V.B. Solid Voxel (Boundary/Surface) Model

Referring now to FIGS. 1A, 1B, 2, 3, 5A, 5B, 9 and 11, in FIG. 5A there is shown an object 160 in boundary solid representation 3D space 192. Object 160 is a B-Rep construct and consists of multiple primitives 194 (e.g., polygons, quadratic surfaces and Non-Uniform Rational B-Splines or "NURBS" surfaces). In FIG. 11 there is shown the pseudocode algorithm 310 used in the voxelization stage 152 by voxelization software 212 to voxelize object 160. For proper operation of algorithm 310, it is assumed that the boundary representations of objects 160 are valid (i.e., the algorithm 310 will not work properly with invalid boundary representations). Thus, as long as the boundary surfaces of primitives 194 of the different objects 160 do not intersect each other, multiple objects 160 may be considered as one solid object 160.

Many of the steps performed by algorithm 310 are similar to those already described for algorithm 300 for solid/curve voxelization, and so will not be described here in detail. Instead, the focus of this section will be on the differences between the two algorithms 300 and 310 and challenges occasioned by voxelizing boundary solid representations according to the method of the present invention. Boundary representations of objects 160 present a particular challenge since the boundary 3D model lacks any information about the interior of the objects 160. The B_Rep construct of objects 160 does contain information about the boundaries of objects 160. Therefore, if algorithm 310 merely proceeded slice-by-slice 180 in a front plane 246 to back plane 248 order like algorithm 300, frame buffer 99 and z-buffer 97 would contain only voxels 94 representing the boundaries of objects 160. To overcome this limitation, algorithm 310 employs the frame buffer blending function feature of OpenGL 3D Graphics API 208, together with a logical XOR operation, to carry the boundary information to the interior of object 160. This approach is based on the principle that when shooting a ray from a pixel to the object space, the entering points and the exiting points on the ray against a solid object always appear in pairs, and the voxels between each pair of entering and exiting points are the interior voxels (i.e., the intersection parity in the z-direction).

To understand this approach, it is important to note that in general (and in OpenGL in particular) for each pixel 95 in a frame buffer 99 there is a color value 120 (shown in FIG. 1B). In particular, each color value 120 is a 24 bit word 122, consisting of three 8-bit words 124. Each 8-bit word 124 represents one of the three color components (e.g., red, green and blue in the RGB color model). Other color representation systems are well know to one skilled in the art, though they may require modification to the bit architecture (e.g., words 122 and 124) of the color value 120. A frame buffer blending function is a function that blends the current pixel 95 color values 120 in the frame buffer 99 and the color values 120 of the incoming pixel 95 to be written to that position in the frame buffer 99.

Figure 12:
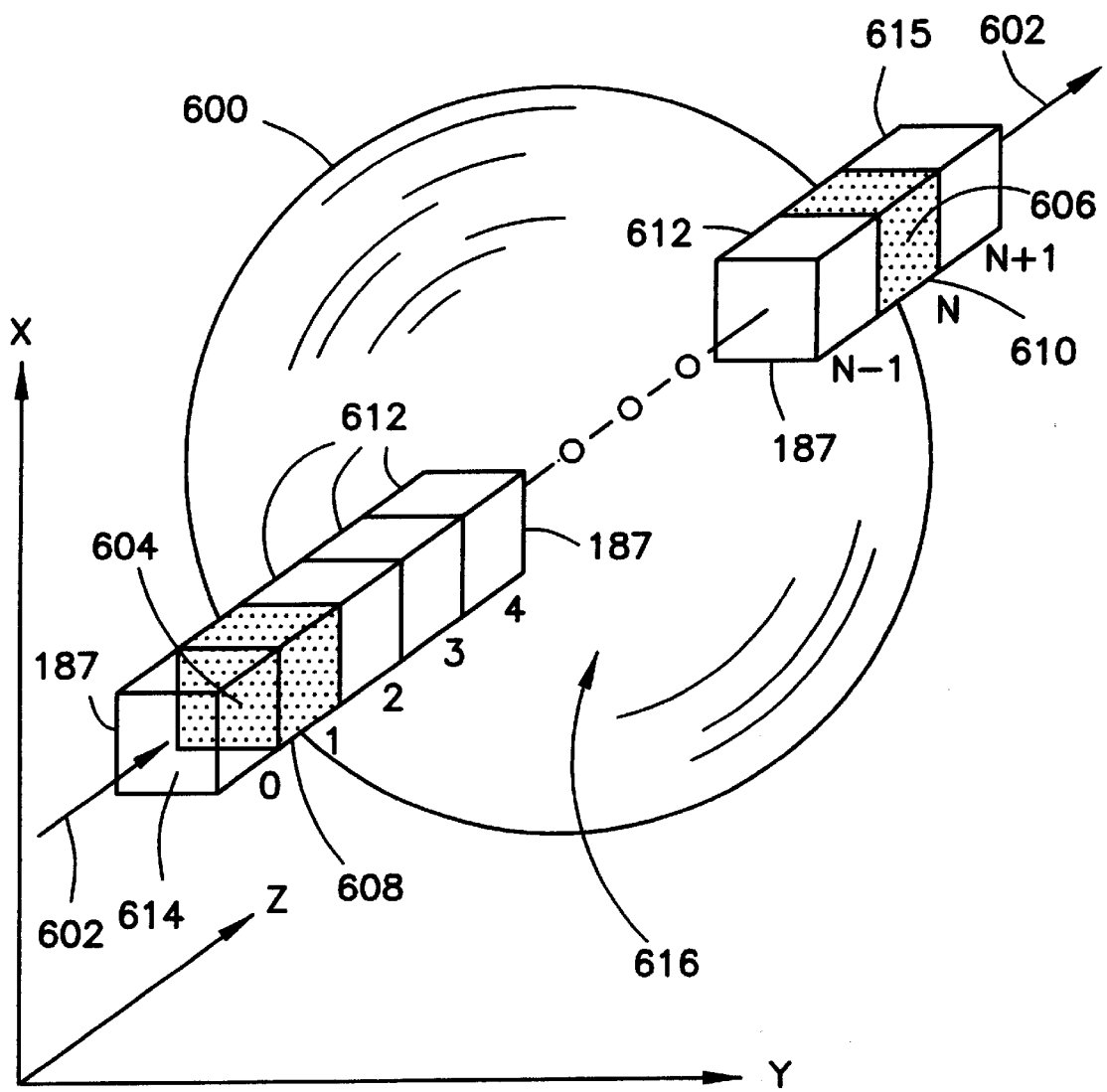
FIG. 12 is a pictorial representation of a solid object in solid boundary 3D space prior to its voxelization according to the pseudocode of FIG. 11.
Figure 14:
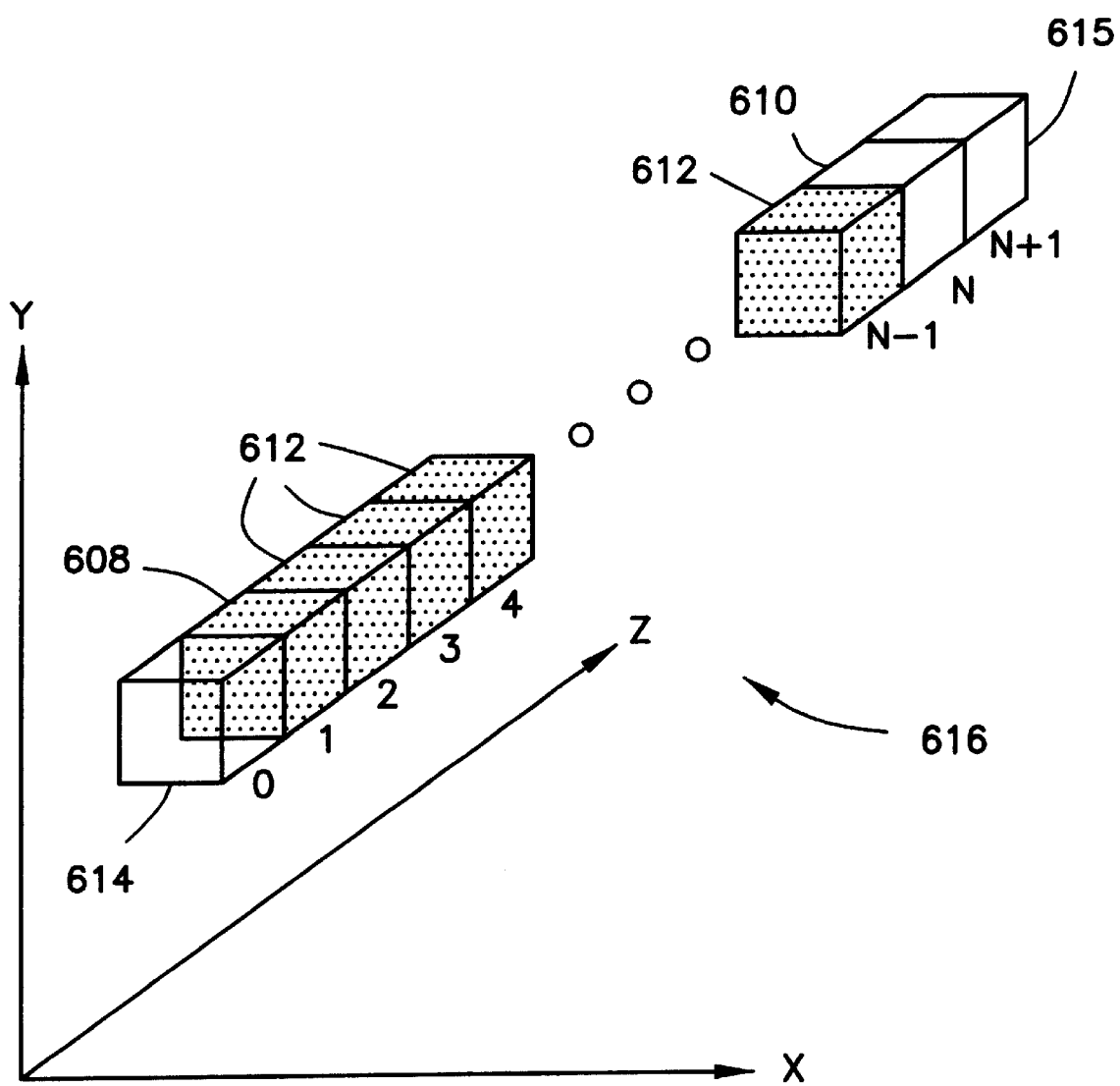
FIG. 14 is a pictorial representation of the solid object of FIG. 12 at a later stage in its voxelization.

Referring now to FIGS. 1, 11, 12, 13 and 14, after initializing in step 312 (similar to step 302 of algorithm 300), in step 314 algorithm 310 clears frame buffer 99, enables the OpenGL XOR function and sets in color value 120 certain colors for pixels 95 in frame buffer 99 to represent the presence and absence of a portion of object 160 boundary in each particular voxel 187 of voxel space representation 189 of B_Rep object 160. This process and the succeeding operations of algorithm 310 are illustrated in FIGS. 12 through 14.

In FIG. 12 there is shown the outline of a B_Rep of solid object 600, here shown as a sphere for simplicity. Note that although object 600 is solid, its B_Rep model portrays it as a hollow shell. Also shown are certain of the voxels 187 of the voxel space 185 into which object 600 will be transformed.

In FIG. 12, ray 602 in the z-axis (the viewing direction) enters object 600 at point 604 and exits object 600 at point 606. Boundary entry point 604 is contained by voxel 608, boundary exit point is contained by voxel 610. Both voxels 608 and 610 are currently shown as shaded to represent that they ideally should contain a portion of the boundary of object 600. Between voxels 608 and 610, ray 602 passes through a series of voxels 612. Together, voxel 608, voxels 612 and voxel 610 form a connected series 616 of n voxels. Also shown to aid understanding is voxel 614, immediately adjacent voxel 608 along the z-axis, which ray 602 passes through before reaching boundary entry voxel 608, and voxel 615, immediately adjacent voxel 610 along the z-axis, which ray 602 passes through after leaving boundary exit voxel 610.

To use frame buffer 99 for voxelization of VCSG objects 160 like object 600 (a process for which buffer 99 was neither designed nor intended), pixel color 120 (0,0,0) is defined as the color of the "background," representing voxels 187 "empty" of any part of the boundary of object 160 (e.g., voxel 614, 615 and voxels 612). Similarly, the pixel color 120 (255, 255, 255), the full color value 120 for a 24-bit word 122 frame buffer 99, is defined as the "surface" or "object" color of pixels 95 representing voxels 187 at the surface of object 160 (that is, representing filled voxels 187 that contain a portion of the surface boundary of object 600, such as voxels 608 and 610). In this manner, an unfilled voxel 187 would have its associated pixel 95 with "0"s in all of its 24 bit word 122 frame buffer 99 position, while a filled voxel 187 would have "1"s in all of its 24 bit word 122 frame buffer 99 position. (Note that to maintain these imposed color values 120, algorithm 310 should disable all the features of OpenGL that may operate on frame buffer 99 to alter the drawing colors. Such features include lighting, shading, anti-aliasing, texturing and alpha blending.)

Applying this color scheme to object 600 in FIG. 12, the pixels 95 in frame buffer 99 corresponding to voxels 608 and 610 should have color value 120 (255,255,255), while all of the other pixels 95 (including those corresponding to voxels 612) should have color value 120 (0,0,0). Yet from the definition of object 600 as a solid object, the desired outcome of the voxelization of object 600 is for the pixels 95 corresponding the voxels 612 to all have color value 120 (255,255,255). How can algorithm 310 achieve this desired results? The key (mentioned previously) is the appropriate use of the OpenGL XOR operation.

Referring now to FIGS. 1A, 1B, 9, 11, 12, 13 and 14, in step 316 slices 180 are generated for the bounding box 240, in front to back plane order as described in greater detail above for step 304 of algorithm 300, but with the OpenGL XOR operation enabled. The net effect is illustrated in the table in FIG. 13 and the pictorial representation in FIG. 14. Since voxel 614 is "empty" ("E" in the table in FIG. 13) of any portion of the surface of object 600, its associated pixel will have a color value 120 of (0,0,0). (Note that similarly, since by definition of object 600, all voxels that ray 602 passes through before reaching voxel 614 will also have color values 120 of (0,0,0). The XOR operation on these voxels and on voxel 614 will yield color value 120 of (0,0,0).) Since voxel 608 is filled, its associated pixel 95 would have a color value 120 of (255,255,255). Before this value is entered in pixel 95, it must be XOR'd to the previous color value 120, which is (0,0,0). The result of this operation is the color value 120 of (255,255,255), which is entered in the table of FIG. 13. Now the next voxel in voxel series 616 is the first of a chain of voxels 612, all of which are empty, and so would have a color value 120 of (0,0,0) associated with their pixel 95. However, the XOR operation applied to this color value 120 and the color value 120 of the previous pixel 95 in the buffer 99 yields an color value 120 of (255,255,255), which is reflected in the table in FIG. 13.

Note that this process yield an anomalous result for the pixel 95 associated with boundary exit voxel 610. After applying this process to the n-1 voxel 612, yielding a color value 120 of (255,255,255), the XOR of this color value 120 with the color value 120 associated with voxel 610 of (255,255,255) yields a color value 120 of (0,0,0) for the pixel 95 associated with voxel 610. One intuitive solution to this missing exit point boundary problem would seem to be to enable anti-aliasing when the initial slicing step is performed in step 316 (which would be similar to step 304 of algorithm 300 for the solid/curve voxelization process, where prior step 302 enables OpenGL polygon and line anti-aliasing). However, this proposed "solution" would invalidate the underlying concept behind step 316, the intersection voxel parity in the z-direction, since such anti-aliasing uses either super-sampling or area sampling.

The missing exit boundary voxels 610 are not the only problem with step 316. When some part of the solid object 600 is thinner than a slice 180 in the z-direction, it is possible that the respective entering and exiting points 604 and 606 fall within the same slice 180. Using the XOR operation of OpenGL, the associated voxels 187 in such a thin region would cancel each other out before the slice 180 is completely entered into the frame buffer 99.

Figure 15:
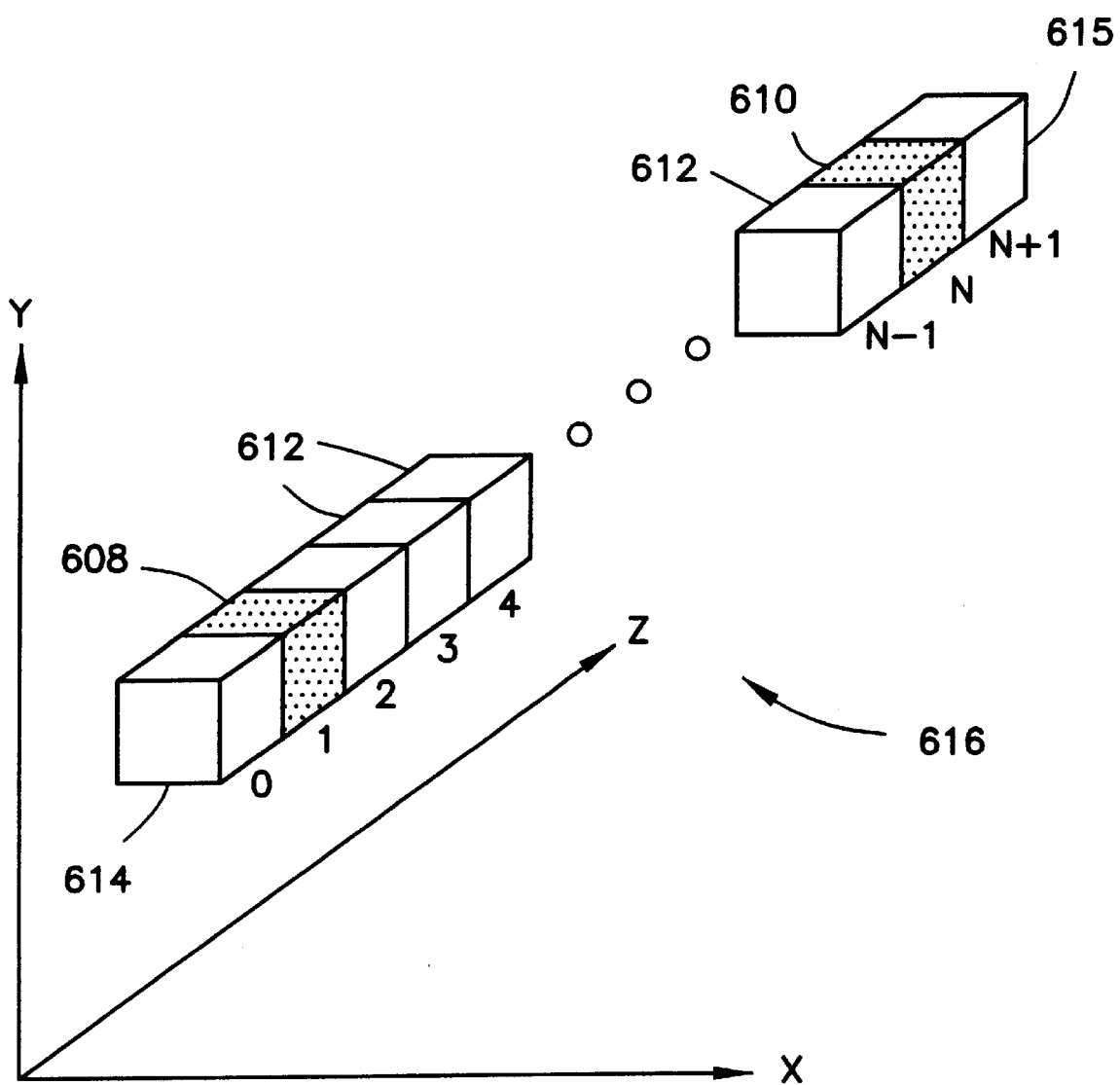
FIG. 15 is a pictorial representation of the solid object of FIG. 12 at a later stage in its voxelization.
Figure 16:
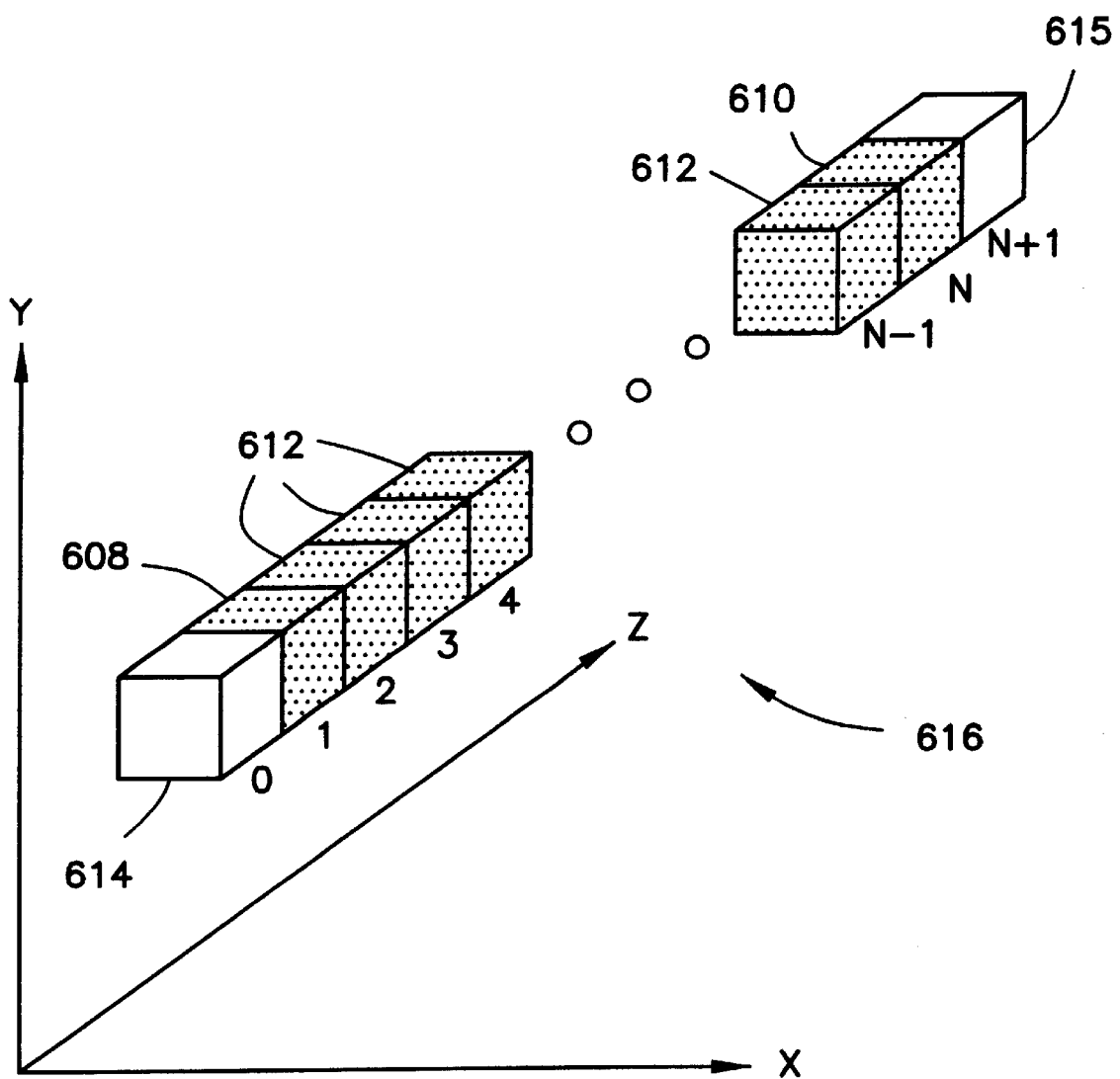
FIG. 16 a pictorial representation of the solid object of FIG. 12 in the last stage in its voxelization.

The solution to both of these two problems is to "superimpose" onto the solid voxelization results achieved by step 316 the complete set of surface boundary voxels (e.g., voxels 608 and 610 from FIG. 12), constructed from the separate surface voxelization procedure outlined in step 318. For the step 318 surface boundary voxelization, anti-aliasing is set in OpenGL: Since with anti-aliasing enabled thin regions are actually degenerated to surfaces in volume representations, the set of all surface voxels 187 will effectively fill any thin regions, as well as any missing boundary voxels (e.g., voxel 610 in FIG. 14). In operation, after each slice 180 of the surface volume is generated in frame buffer 99 in step 316, in step 318 the same slice 180 from the solid volume (created in step 316) is also drawn to the frame buffer 99 using OpenGL 3D texture mapping and an OpenGL logical OR blending function, which effectively merges the two slices 180 into one. This is illustrated for object 600 in FIG. 16, which shows the result of OR'ing together the solid volume representation of FIG. 14 with the boundary representation of FIG. 15.

V.C. VCSG Model

In this section two separate approaches to handling VCSG Models are described. The first approach is to treat all 3D models as scalar models. This approach can lead to greater resolution of objects rendered into 2D. The second approach recognizes that in some applications only solid objects are considered (e.g., CAD/CAM application 410 shown in FIG. 8). Converting the scalar 3D model to a binary 3D model before voxelization can dramatically speed up the voxelization process. Of course, absent other measures the scalar to binary conversion discards information about the object and can lead to less accurate 2D display of the object. In many applications, however, the increased speed of voxelization more than compensates for any degradation of the 2D object display.

V.C.1. Scalar Approach.

Figure 17:
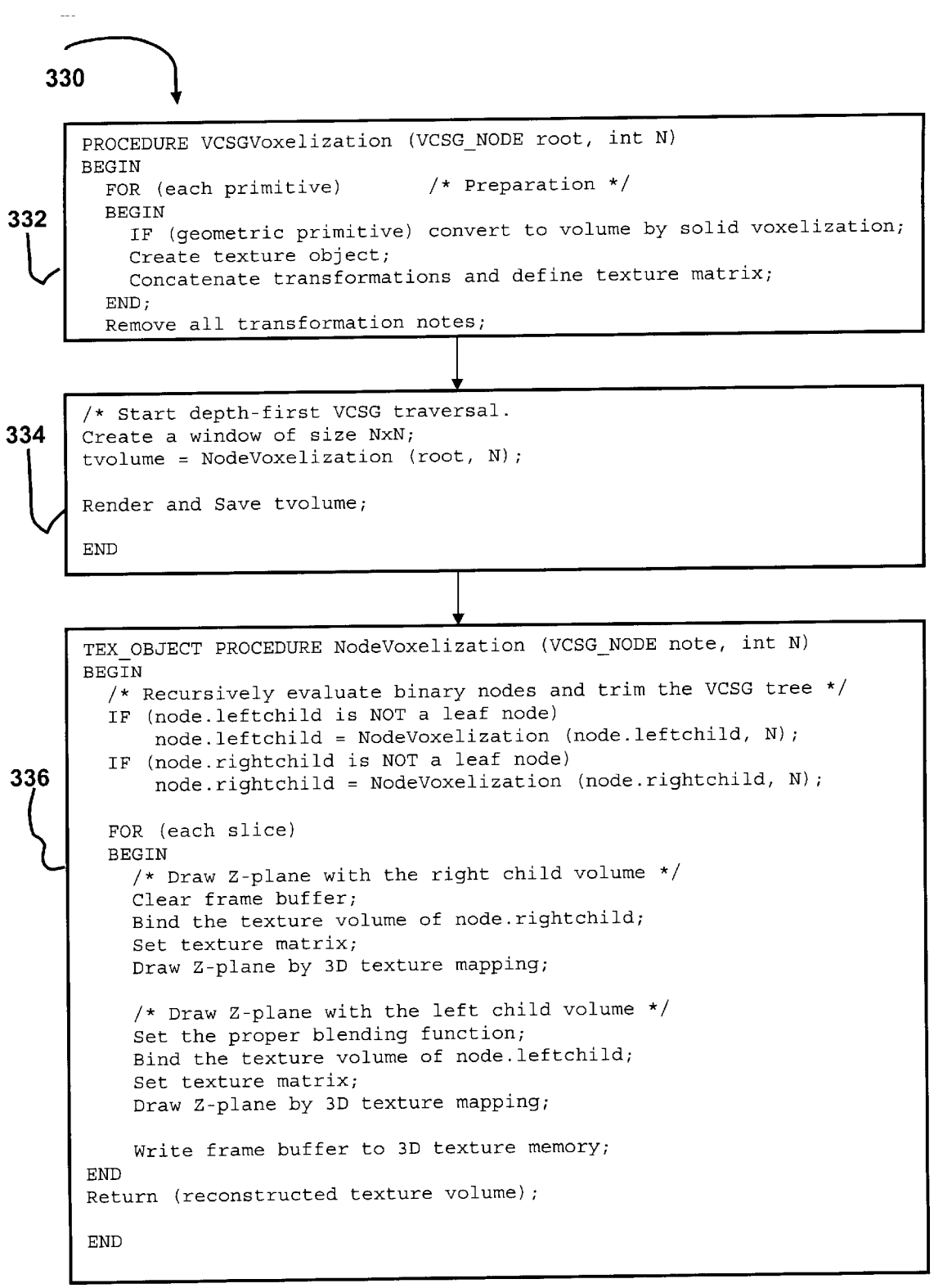
FIG. 17 is a flow chart of the pseudocode used to implement the present invention for objects in VCSG 3D space.

Referring now to FIGS. 1A, 1B, 2, 3, 6A, 6B, 9, 17, 18, 19 and 21, the scalar approach will be illustrated first. In FIG. 6A there is shown an object 160 representative of all objects in VCSG space 193. In FIG. 17 there is shown the pseudocode algorithm 330 used in the voxelization stage 152 by voxelization software 212 to voxelize object 160. Many of the steps performed by algorithm 330 are similar to those already described for algorithms 300 and 310 for solid/curve voxelization and boundary/curve voxelization, respectively, and so will not be described here in detail. Instead, the focus of this section will be on the differences between algorithm 330 and the two other algorithms 300 and 310.

It is important to recall that the CSG representation allows users to define complex 3D solid objects 160 by hierarchically combining simple geometric primitives (not shown) using Boolean operations and affine transforms. A natural extension of the CSG method is to allow volume datasets (e.g., the results of MRI 404 or CT 402 scans, shown in FIG. 8) to be used as CSG primitives, and at the same time to allow the intensity values of the volume datasets to be computed during Boolean operation. Such models are called Volumetric CSG models, or simply VCSG models.

Figure 18:
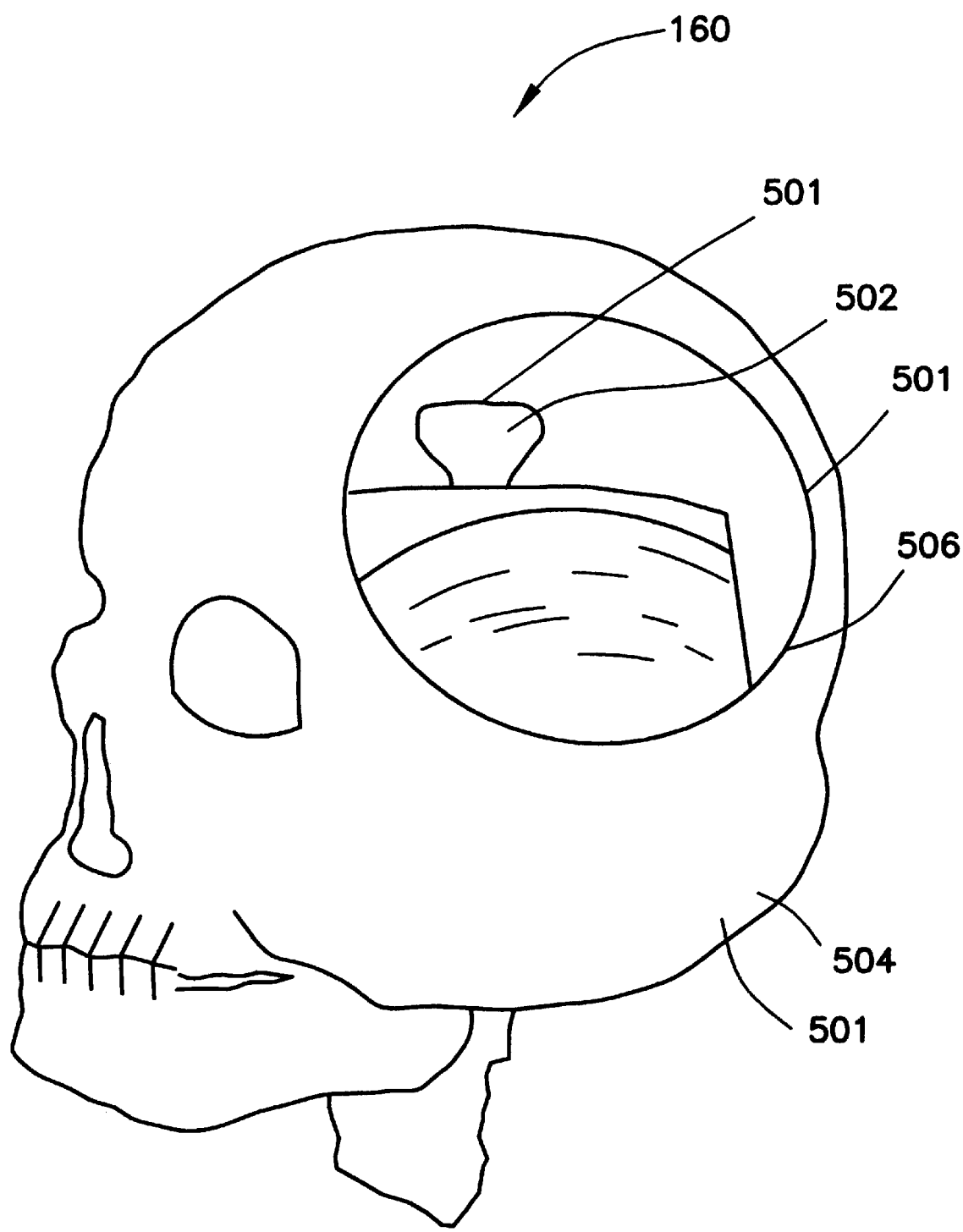
FIG. 18 is a pictorial representation of three objects in VCSG space prior to voxelization in accordance with the method of the present invention.

Among the challenges in voxelizing objects 160 in VCSG space 193 is that an object 160 may be composed of multiple primitives (not shown), each of which may be of one of a few possible 3D representations. To illustrate this challenge, voxelization of a more detailed object 160 will now be considered. Referring now to FIG. 18, there is shown an object 160 composed of three primitives 501, a teapot 502, a human skull 504 and a sphere 506. Associated with this object is a VCSG tree 510, shown in FIG. 19. As is well known to those skilled in the art, tree 510 is a convenient notation for representing the data structures underlying object 160, including the formats and interrelations of the primitives 501 that compose object 160. In particular, tree 510 consists of three leaf nodes 512, one for each primitive 501. Two leaf nodes 512 combine at a Boolean node, such as Boolean nodes 515 and 516, where Boolean relationships define the interaction between the primitives 501 represented by the two respective child nodes meeting at Boolean nodes 515 and 516.

To have a uniform representation for all CSG primitives 501, all geometric primitives 501 are first converted into volume representations by solid voxelization. Afterwards, the VCSG model will only have such volumes as primitives 501 at the leaf nodes 512. In tree 510, this transformation is represented by the letter "T" at nodes 514. After transformation at nodes 514, the primitives 501 can be combined as required using Boolean operations. For example, in FIG. 19, teapot 502 is in Union 516 with skull 504, as indicated by Boolean node 516. This resulting primitive is then in Intersection 518 with sphere 506, as indicated by its Boolean node 515.

Boolean operations for volumetric objects 160 can be defined as "voxblt" operations, as described in "The Voxblt engine: A voxel frame buffer processor" by A. Kaufman in A. A. M. Kuijk, editor, Advances in Graphics Hardware III, ApringerVerlag, pp. 85–202, 1992, and incorporated herein by reference, or fuzzy set operations, as described in "Volume-sampled 3D modeling,". IEEE Computer Graphics and Applications, 14:26–32, by Sidney Wang and Arie Kaufman, and incorporated herein by reference. In addition, for the Boolean operations of Union and Intersection, the intensity values of the two volume objects 160 under operation also need to be blended in their overlapping regions. This is preferably accomplished by associating with each Boolean operation an intensity function, V0, that blends the two intensity values (one per object) into one intensity value. For binary volumetric objects 160, combining the intensity values is a simple binary logic function. In contrast, for scalar volumetric objects 160, combining the two intensity values is more complex. As discussed further below, the method of the present invention combines intensities for scalar volumetric objects 160 using the blending functions of the texture mapping feature supported by OpenGL or other Graphics API 208 and associated graphics accelerator 114.

In interactive applications, the VCSG models often are frequently modified (e.g., due to manipulation of the objects 160) by a user. Each modification requires a new voxelization of the entire VCSG model for volume rendering. As a consequence, a fast VCSG voxelization algorithm is essential for providing volume rendering support for interactive VCSG modeling. In accordance with the method of the current invention, this is achieved using hardware acceleration capabilities of graphics accelerator 114 in a novel manner. Among other things, with the VCSG representation, advantage can also be taken of the texture memory 109, which allows the Boolean operations to be performed on a voxel-by-voxel basis during voxelization. This collapses the process of rendering a CSG tree, such as tree 510 shown in FIG. 19, to a 1D Boolean operation between pairs of voxels before volume rendering.

Referring now to FIGS. 1A, 1B, 9, 17, 18 and 19, the Boolean operations in tree 510 required to generate the corresponding image in FIG. 18 are performed using frame buffer blending functions available in graphics accelerator 114 and software 200. In accordance with another aspect of the present invention, the slicing process (illustrated in FIG. 9 and accompanying text) and transformation operations are performed using 3D texture mapping available in graphics accelerator 114 and software 200. (Note that graphics accelerator 114 and graphics API software 208 are not designed nor intended to be used in these manners.)

In operation, in step 330 for each primitive 501, if it is not already a volume representation (e.g., a geometric primitive, such as sphere 506), the primitive 501 is first converted to volume representations by means of solid voxelization. Preferably, this conversion is accomplished using the method of section V.B. Solid Voxel (Boundary/Surface) Model, above. Then the volume primitive is converted into a 3D texture object. This is done by concatenating the sequence of transformations 514 applied to each primitive into one cumulative transformation matrix, and then storing its inverse with the primitive as a texture matrix. This approach takes advantage of the fact that with 3D texture mapping, when a texture matrix is enabled, all texture coordinates are transformed by the texture matrix first, prior to the texture mapping process. This achieves exactly the same effect as the geometric transformation operations defined in the VCSG model, but using the texture mapping hardware capability of accelerator 114.

Figure 20:
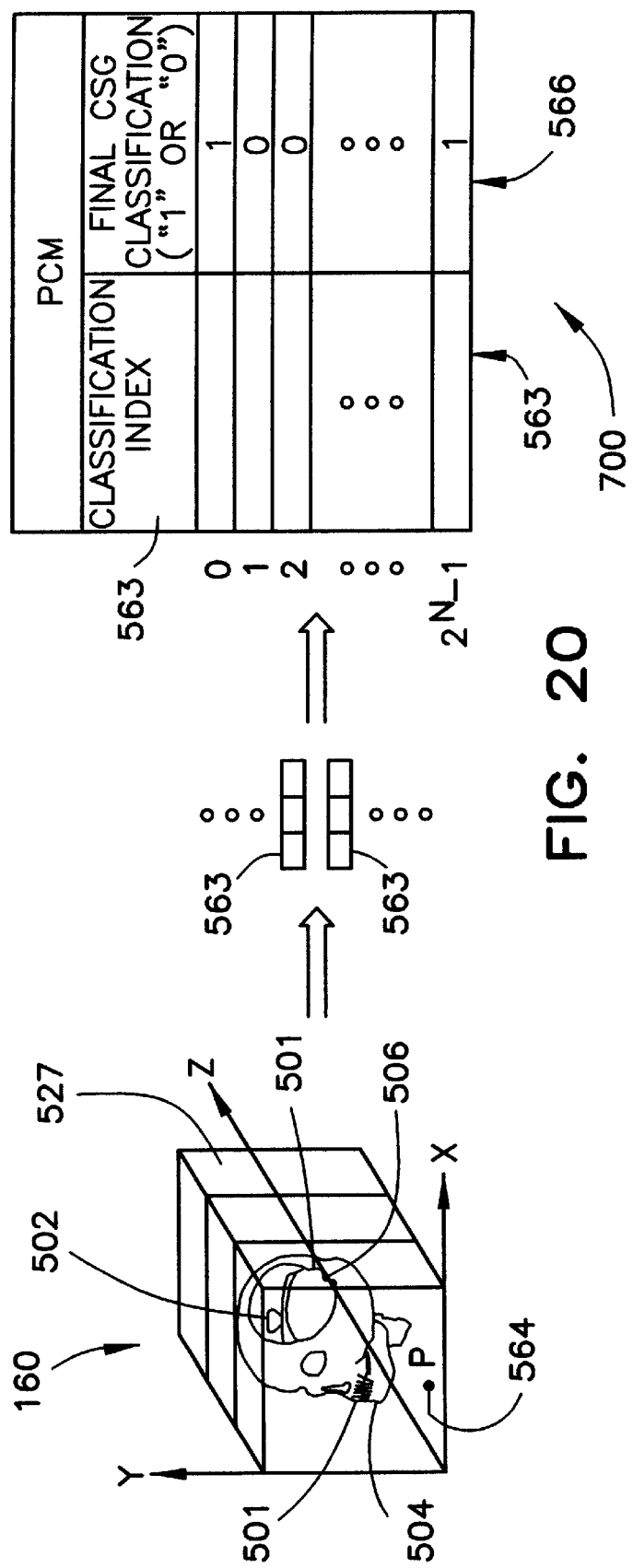
FIG. 20 is a pictorial representation of the texture mapping slice operation performed by the pseudocode of FIG. 17.

Referring now also to FIG. 20, next in step 334 the Boolean (binary) nodes 515 in tree 510 are evaluated one by one, based on a depth-first traversal of tree 510. Each Boolean operation generates a new 3D texture object or volume 520 which replaces the leaf or subtree 512 under its associated Boolean node 515. The texture volume 520 is generated slice by slice (not shown) using a slicing process similar to that used by the solid voxelization depicted in FIG. 9 to generate slices 180 in bounding box 240. Given the substantial similarities between these processes, details of the geometry of slice generation will be omitted here.

In brief, each slice 522 is taken perpendicular to viewing direction 274 and slices both primitive object texture volumes 520 subject to the particular Boolean node 515 (e.g., skull and teapot texture volumes 520 in FIG. 20). For each slice 522, its central Z-plane is generated by 3D texture mapping by accelerator 114 with the two texture volumes 520, respectively, and the resulting two slices 523 of images 524 (shown in FIG. 21, but only one slice of each is shown for simplicity) are blended together in frame buffer 99 using the appropriate blending functions described further below. The resulting frame buffer image 526 is then written into texture map 105 of memory 109 as one slice 521 of the new, intermediate, texture object 527.

Figure 21:
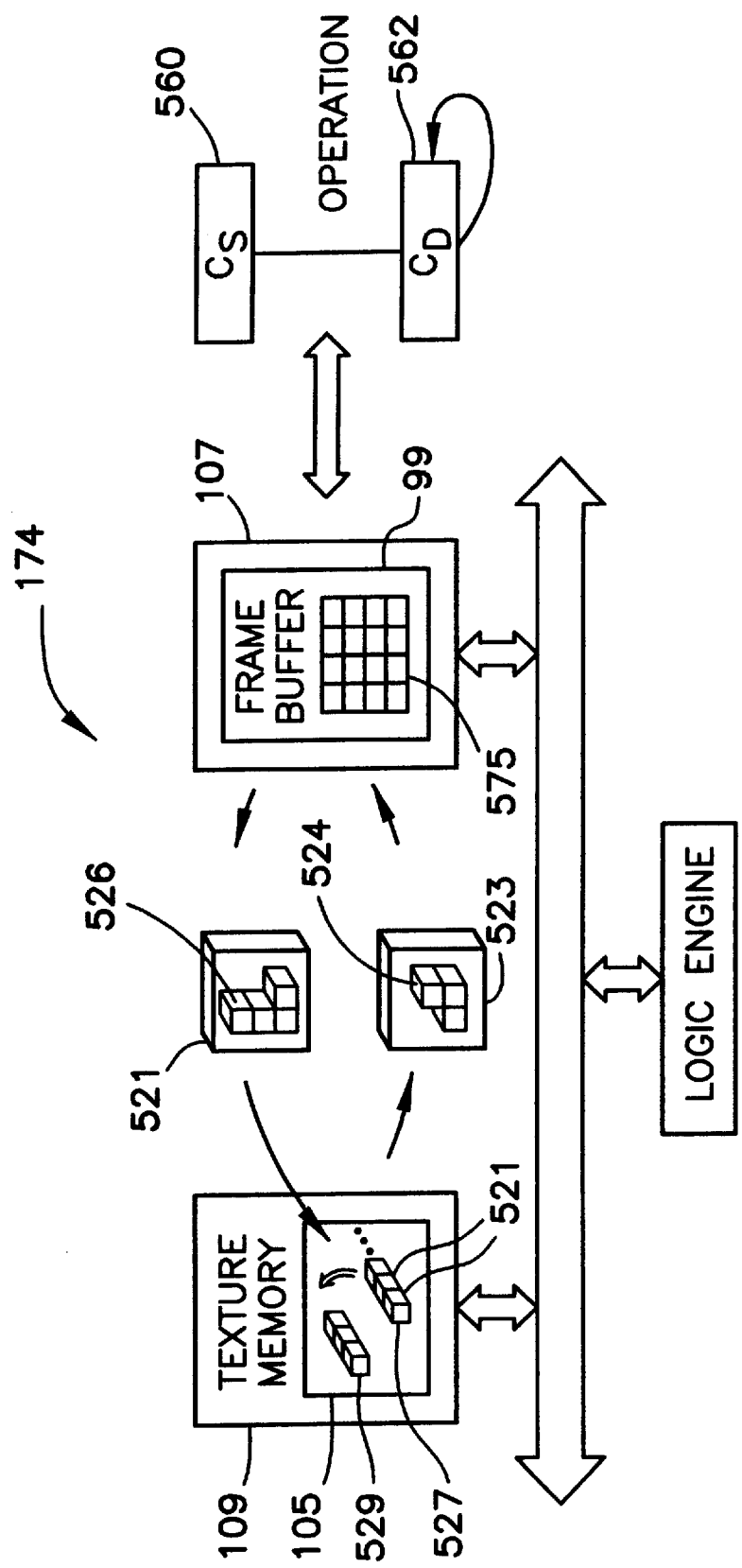
FIG. 21 is pictorial representation of a portion of the graphics hardware of the system of FIG. 1, illustrating certain steps of the pseudocode of FIG. 17.

Next, in step 336 the VCSG tree of the intermediate texture object 527 is recursively trimmed, one branch at a time, to generate the final VCSG volume. The final volume can then be rendered by 3D texture mapping. In step 336, blending functions are used to combine the slices of images 524. As shown in FIG. 21, the typical function of frame buffer blending functions in graphics accelerator 114 and Graphics API software 208 (shown in FIG. 2), such as OpenGL, is to combine a color value 560 from a source (incoming pixel) and the existing color value 562 in the frame buffer 99 (destination). In particular, let Cd denote a frame buffer color (destination color) 562 and Cs denote the incoming pixel color (source color) 560. In OpenGL, a blending function takes the following form:

$$C=(Cs*Fs)(\text{Operation})(Cd*Fd)$$

where Fs and Fd are called source and destination factors, respectively, C is the output color written back to the frame buffer, and Operation is the equation operation chosen from several different options, such as addition, subtraction, Min-Max and logical operations. In accordance with one aspect of the present invention, in step 334 the combinations of coefficients and equations was used to perform Boolean operations directly in the frame buffer 99, for two images 523 (FIG. 21) drawn from the same slice 522 (FIG. 20) drawn from separate primitives 501. Since OpenGL blending functions are implemented in hardware in graphics accelerator 114, this approach of the present invention provides a relatively fast Boolean operation evaluation method with scalar volumes.

The following Boolean operations can be implemented using the apparatus of FIGS. 1A and 1B, together with the listed OpenGL (or other graphics API software 208 having similar features and functions) commands:

Union Operation:
C=Max(Cs-Cd, 0), where subtraction is the OpenGL command. Note that any non-zero destination color should be turned to the full color ((1,1,1) or (255,255,255) depending on the particular color format) by a color table to ensure a full subtraction.

V.C.2. Binary Approach (When Voxelizing, treat all 3D objects as solids

Referring now to FIGS. 1A, 1B, 2, 3, 6A, 6B, 9, 18, 19, 23, 24, 25 and 26, in FIG. 18, there is shown an object 160 representative of all objects in VCSG space 193. Object 160 is composed of three primitives 501, a teapot 502, a human skull 504 and a sphere 506. Associated with this object is a VCSG tree 510, shown in FIG. 19. As is well known to those skilled in the art, tree 510 is a convenient notation for representing the data structures underlying object 160, including the formats and interrelations of the primitives 501 that compose object 160. In particular, tree 510 consists of three leaf nodes 512, one for each primitive 502, 504 or 506.

Many applications require the display of a 2D object representation 301 rendered from a 3D scalar model (not shown) of an object 160. That is, for each coordinate point in the object 160 there is associated a scalar value. In contrast, a binary volume (a/k/a "solid object", such as sphere 506) is a volume having only a logic "0" or "1" intensity value for each point, with "1" representing a point inside a 3D object 160 and "0" representing a point outside the 3D object 160.

In general, rendering a 2D object representation 301 from a scalar 3D model of an object 160 is more time consuming for a given computer system 100 than for rendering such a 2D object representation 301 from an analogous binary 3D model. In some applications (e.g., CAD/CAM application 410 shown in FIG. 8), the 2D object representation 301 need not be displayed with the precision or accuracy inherent in the 3D scalar model. For these applications, the method of the present invention first converts any and all 3D models to binary 3D model representations in a relatively fast manner. The result of this conversion process is basically a binary volume representation of the generalized CSG model, with an error tolerance of the dimensions of a voxel. In solid modeling, such binary volume is also called the "spatial enumeration representation." Then, voxelization is performed essentially using the method described above in Section V.A. Curve/Surface Model.

Referring now to FIGS. 23 and 24, in FIG. 23 there is shown the pseudocode algorithm 730 used in the voxelization stage 152 by voxelization software 212 to voxelize object 160. Algorithm 730 calls procedure call 732 to perform certain key calculations, as discussed further below. Once such a binary (solid) representation is obtained, algorithm 300 (solid/curve voxelization) can be used for voxelization. Although algorithms 300 and 730 have different objectives, many steps performed by algorithm 730 are similar to those already described for algorithm 300 for solid/curve voxelization, and so will not be described here in detail.

Referring now to FIGS. 1A, 1B, 2, 3, 6A, 6B, 9, 18, 19, 23, 24, 25 and 26, at the heart of this binary voxelization approach is the need for a relatively fast method to convert from classification of primitives 501 composing a CSG object 160 to classification of the CSG object 160 itself. As will be seen, this method uses a novel approach that takes advantage of Dual Use Technology. Before describing how Dual Use Technology is used, an overview of the conversion method will be given.

In essence, with the scalar-to-binary conversion method first a classification operation is performed on each point P 564 (shown in FIG. 20) in the 3D space. For each such point 564, it is determined whether the point 564 is inside or outside each primitive 501, such as teapot 502, that makes up an object 160. Note that this is not the same as mapping each point 564 to the object 160 itself, since it is possible for a point 564 to inside a particular primitive 501 but outside the overall object 160 (e.g., this would be the case if the Boolean operation relating the particular primitive 501 to the object 160 is the subtraction of the particular primitive 501 from other primitives 501 comprising the object 160). The results of this classification is an n-bit word 563 (shown in FIG. 20) associated with each point 564, where "n" is the number of primitives 501 composing an object 160. In particular, let n be the number of leaf nodes (primitives or subtrees) 501 in a CSG tree 510. If the n primitives 501 are numbered from 0 to n, then an arbitrary n-bit number 563 can be used to encode the classification results of a point 564 against all n primitives 501. This binary number 563 is called the "Classification Index" of the point 564. A "1" at the jth bit of the Classification Index 563 indicates that the point 564 is inside the jth primitive 501, and a "0" indicates the point 564 is outside this primitive 501.

Figure 19:
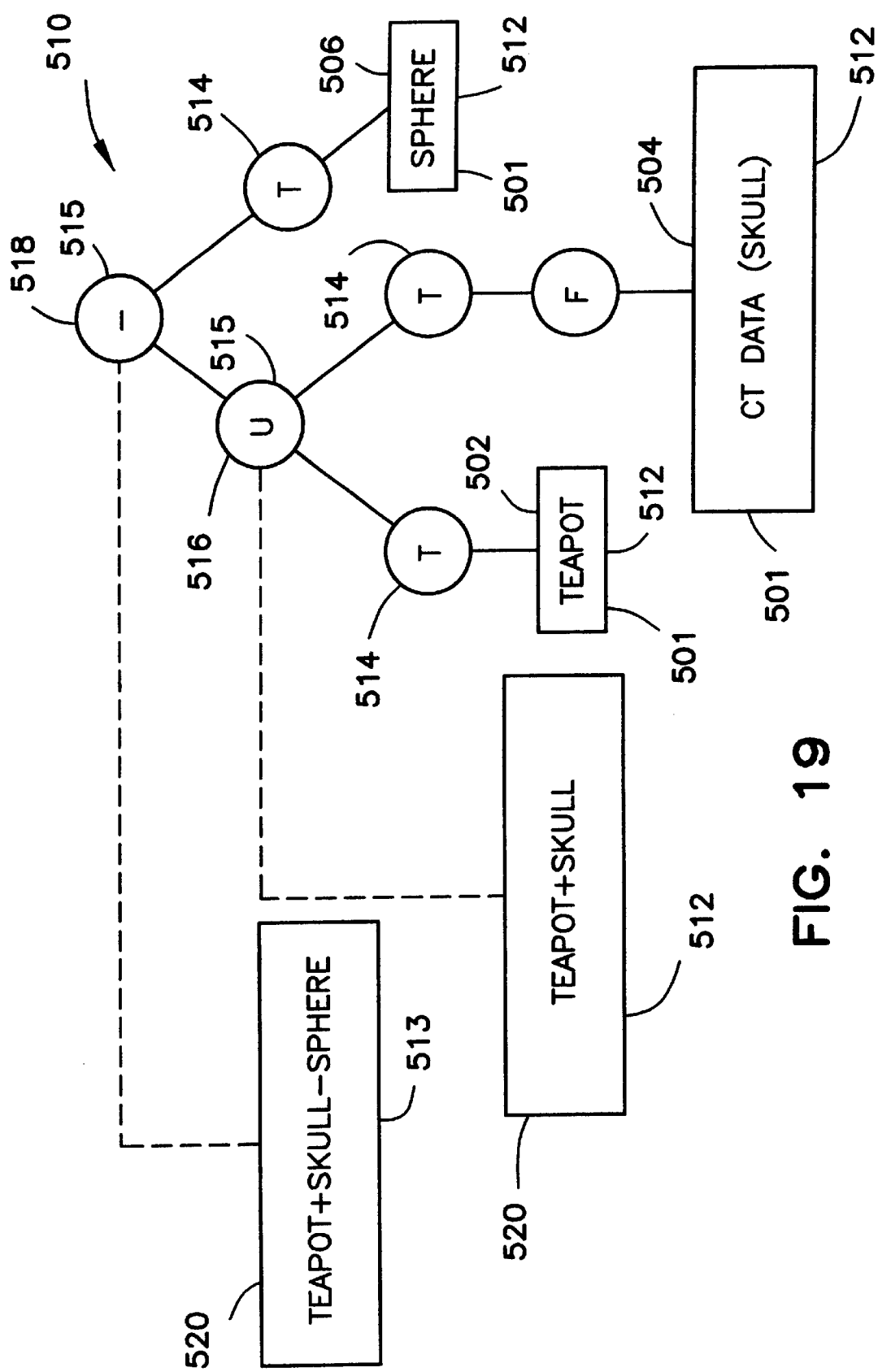
FIG. 19 is a depiction of the CSG tree for the objects in FIG. 18.

As shown in FIGS. 19 and 20, for a given CSG tree 510, each Classification Index 563 uniquely determines the resulting "in/out" classification of the point 564 against the CSG object 160. Thus, all points 564 having the same Classification Index 563 will have the same final CSG classification 566. Since there are only $2^n$ possible different Classification Indices 563, a look-up table 700 of $2^n$ entries will be sufficient to describe all possible point classification cases. This look-up table 700 is, in essence, a Point Classification Map, or PCM 700, that maps a Classification Index 563 to a zero-one classification against the generalized CSG model of an object 160.

Figure 25:
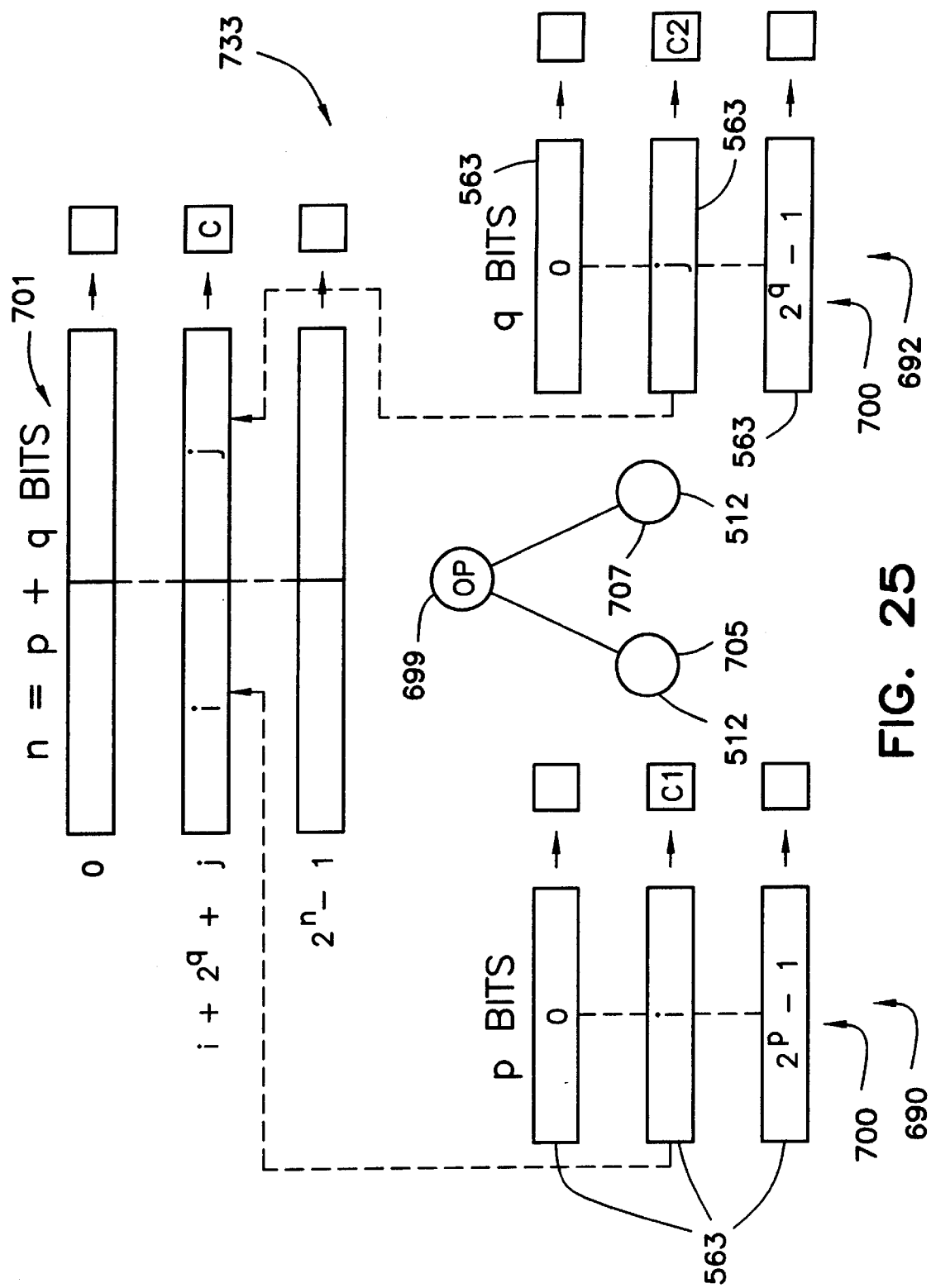
FIG. 25 is a block diagram of one of the operations underlying a module of pseudocode of FIG. 23.

Referring now to FIGS. 19, 25 and 26, once PCM 700 is built, the point classification problem against a generalized CSG model becomes a simple point classification problem against all the primitives 501 (i.e., computing the Classification Indices 563). That is, the PCMs 700 of all the primitives 501 are next combined to form the single PCM

700 of object 160. The PCM of object 160 will essentially be a binary representation of object 160.

As shown in the diagram in FIG. 25 and described in algorithm 732, the PCM 700 of object 160 is calculated recursively by combining the associated PCMs 700 of successive binary pairs of child nodes 512 in VCSG tree 510 until the last two child nodes 512 are combined into a single leaf node 513. How these PCMs 700 are combined is a function of the particular Boolean function joining the two child nodes 512. Typical Boolean functions include Union, Intersection and Subtraction. As shown in FIG. 25, this operation is shown generally as the combination of left and right child nodes 705 and 707, respectively, into binary or parent node 699. The respective PCMs 690 and 692 of left and right child nodes 705 and 707 are combined into the PCM 701 of the binary node 699 by forming the Cartesian product of the Classification Indices 563 of the PCMs 690 and 692 using the Boolean Operations Table 780 of FIG. 26. The combined PCM 701 has a Classification Index domain (as a set of tuples of bits). Note that for a node 699 that is a leaf node, the Boolean Operations Table 780 would be a simple 1-bit, 2 entry table that maps "1" to "1" and "0" to "0".

Referring now to FIGS. 18 and 23, the first step 742 of algorithm 730 removes all the transformation nodes (denoted by a "T") in the VCSG tree 510 of object 160 by concatenating all the transformation operations (e.g., Union and Intersection) applied to each primitive 501 and storing the cumulative transformation matrix as the primitive 501 itself. A primitive 501 will be transformed by its cumulative transformation before it is voxelized in a later step. This can be accomplished through the transformation matrix stack (not shown) of 3D graphics API software 208, such as the MODELVIEW matrix stack in OpenGL. Similar to the "slice by slice" point made above, this also allows the point classification process to be carried out in the same coordinate system that will be used after all transformations. Next, in step 744 texture memory 109 (shown in FIG. 1B) is initialized by defining texture objects for each primitive 501.

Next, in step 746 each primitive 501 in object 160 is assigned a unique color value or code 120. In particular, if the CSG tree, such as tree 510, has n primitives 501, then n different color codes 120 are assigned to different primitives 501 so that the color code 120 of the jth primitive 501 is a binary number with the jth bit set to "1" and all other bits set to "0." That is, for a particular spatial point P 564, the color value 120 of P 564 with respect to the jth primitive, $C_j(P)$, is defined as the color value 120 of the jth primitive 501 if P 564 is inside the primitive 501, and 0 otherwise. Note that now in a later step if the series $C_1(P), C_2(P), \ldots, C_n(P)$ is combined in logic engine 101 of graphics accelerator 114 using a logical operation OR or XOR, the result, C(P), is exactly the "Classification Index" 563 of point P 564.

Next, in step 748 algorithm 732 is initialized (pcm= CSG_PCM(root)) and frame buffer 99 is cleared to prepare it for use.

Referring now to FIGS. 18, 19, 20, 24, 25 and 26, in step 752 of algorithm 730 the Classification Index 563 for each point 564 is preferably created using the same slice-by-slice approach used in algorithm 300 for voxelization and depicted in FIG. 9 and described in the accompanying text. Indeed, after algorithm 730 completes the binary conversion process, algorithm 300 will be used to perform voxelization. Using the same coordinate system for the slice-by-slice binary conversion approach of algorithm 730 facilitates the later use of the binary conversion results by the solid object voxelization of algorithm 300. When slicing is done Z-plane to Z-plane, slices 522 of the primitives 501 are displayed and composited onto the frame buffer 99 in a front-to-back order. Properly setting the color values 120 of the primitives 501 (as described above) and the appropriate frame buffer blending functions in graphics accelerator 114 actually generates the Classification Indices 563 for the points 564 in each slice 522 in the frame buffer 99.

Next, in step 754 the creation of the PCM 700 for the final volume can be done in graphics accelerator 114 using a hardware implemented pixel map 575 to create the table 780 of FIG. 26, essentially a color look up table for frame buffer 99 pixels 95. In particular, once the Classification Indices 563 are generated in frame buffer 99 for the points 564 in each slice 522, the PCM 700 can be applied to the image 524 in the frame buffer 99 to generate the final classifications 566 against the entire generalized CSG model for this slice 522. Next, in step 754 each of these final classification-resulting slices 521 will then be copied to the texture map 105 of texture memory 109 as one slice 521 of the final volume 529.

Using the pixel map 575 of the frame buffer 99, the above two steps 754 and 756 can be combined into one step. The pixel map 575 is a hardware-implemented look-up table that maps the color value 120 of each pixel 95 on the current frame buffer 99 to a new color value 120. Once defined, the pixel map 575 can be invoked by any frame buffer image operation, including the copy operation from the frame buffer 99 to texture map 105. That is, the PCM 700 can be automatically applied during the process of copying the frame buffer image 526 into the texture map 105. This process can then be repeated for each slice 521, leading to a complete volume representation 529 in 3D texture memory 109 for the entire generalized CSG model of an object 160.

Referring now to FIGS. 1B and 13, typically, graphics accelerator 114 and other components of computer system 100 have certain hardware limitations that require "workarounds" to implement the first preferred embodiment of the present invention. In particular, the bit depth of the color value 120, which is word 122 of frame buffer 99, is typically limited to 8 to 32 bits. The common RGBA color representation of color value 120 in frame buffer 99 has 8 bits for each word 124 representing each component of RGB color and another 8 bits for the alpha channel. The frame buffer pixel map 575 (shown in FIG. 21) used to implement the PCM 700 can only have separate look-up tables for individual RGBA components. Thus, there can only be four look-up tables of 256 ($2^8$) entries (one for each of the four words 124 in the RGBA color representation), but not any cross combinations among these separate 8-bit words 124 for each color value 120 in word 122. For this typical computer system 100, the basic voxelization algorithm 730 can only handle a CSG tree 510 with eight primitives 501 (i.e., using only one color component or word 124 of the word 122 in the frame buffer 99 and the corresponding pixel map 575).

To overcome this limitation, the second preferred embodiment of the present invention would either build a custom graphics accelerator 114 accommodating more than 8 bits per color component of color value 120 or having the ability to create cross-combinations among the color component words 124 in each word 122 of color value 120. Alternately, the first preferred embodiment uses the existing computer system 100 with a multipass approach. The multipass approach would repeatedly apply the basic volume conversion algorithm 730 to subtrees of the CSG tree 510. At each step a subtree with at most 8 primitives 512 would be chosen and voxelized into a texture object in 3D texture memory 105. This texture object would then be used to replace the entire subtree as a new volume primitive. Repeating this process would lead to an iterative trimming of the CSG tree 512, which eventually would be small enough to directly voxelize.

One downside of this multipass approach would be a speed penalty from the extra data traffic between the frame buffer memory 107 and the texture memory 109. Another drawback is that it puts increased demands on texture memory 109, since several intermediate volumes may need to be stored in the texture map 105, potentially causing more frequent swapping of texture memory 109. To reduce the number of intermediate volumes, the multipass approach could be designed to always choose from among the remaining subtrees the one with the most number of volume primitives 512, so that the old volumes can be replaced by the newly generated volume.

Note that although the result of the PCM mapping is a zero-one classification, different color values 120 can still be defined for each entry of the PCM 700. This is because the 3D texture volume of texture memory 105 can store all four RGBA color components, which means that the PCM 700 could be easily extended to contain color and opacity values as part of the mapping results. This is particularly important in conceptual design where users need to visually keep track of the different primitives 501 and their different combinations during the process of CSG construction.

VI. 2D Display

Referring now to FIG. 3, the 2D display process 156 is performed after the volume rendering stage 154 described above. Several techniques to display representations 301 on display monitors 110 are well known to those skilled in the art, and so the subject will not be treated here in any detail. Typically the display process is performed by a dedicated hardware device located in display interface 108. Monitors 110 can include computer monitors with progressive scan, or television monitors with raster scan.

VII. Alternatives to Volume Rendering and 2D Display

Figure 22:
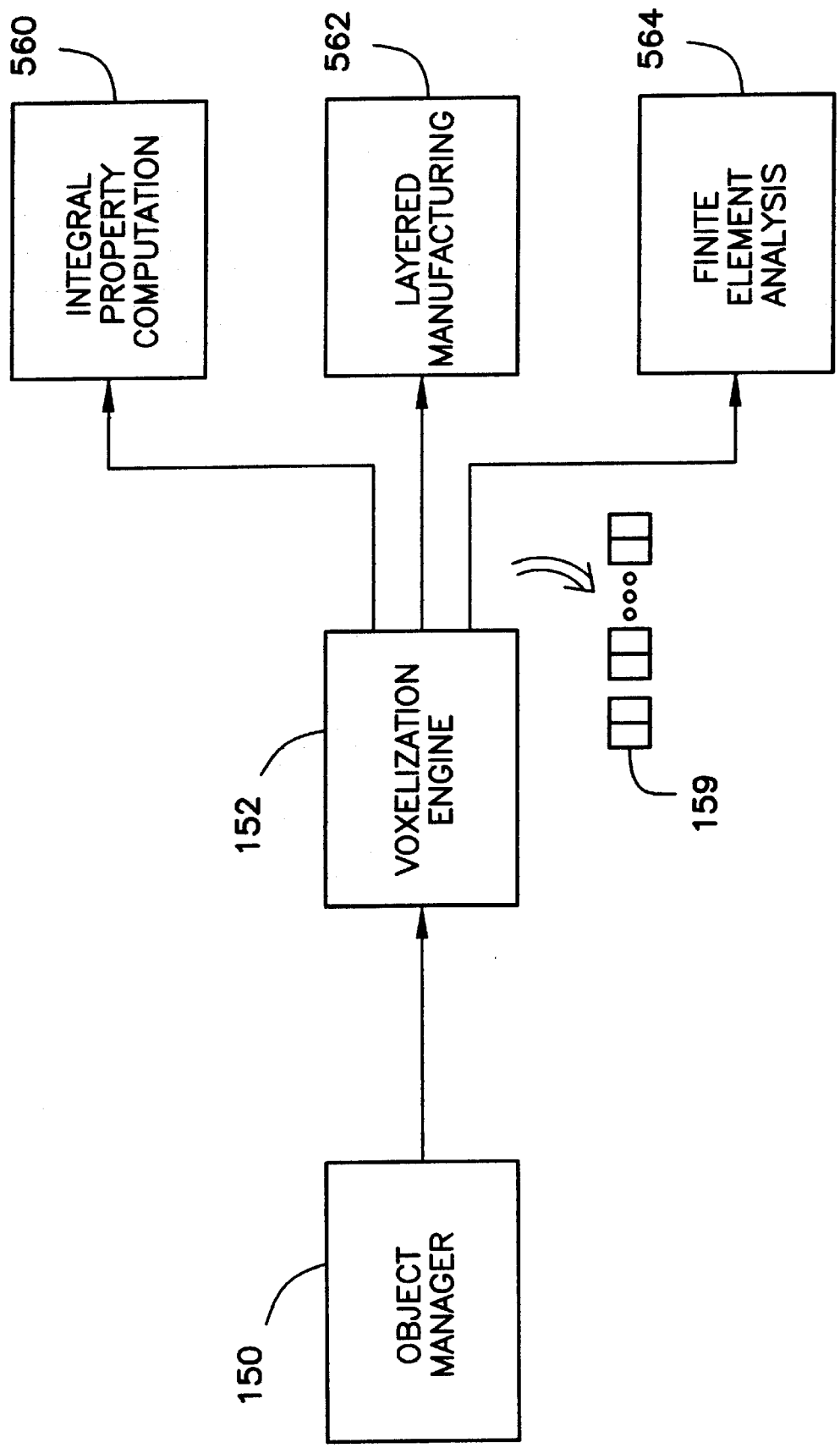
FIG. 22 is a block diagram of an alternate configuration of the method of the present invention depicted in FIG. 3.

Referring now to FIGS. 1A, 1B, 2 and 22, in FIG. 22 there is shown a block diagram of the stages of another embodiment of the method and apparatus of the present invention, implemented on the computer system of FIG. 1 using the software of FIG. 2. This embodiment uses the object manager stage 150 and the same voxelization engine 152 as previously discussed. But from voxelization engine 152, voxelization data 159 (representing the voxelized object) is not routed to volume rendering stage 154 (as shown in FIG. 3), but rather is routed to an application program, such as integral property computation 560, layered manufacturing 562 or finite element analysis 564.

Integral property computation 560 performs operations on the data underlying the voxelized object. Typical examples include surgical simulations. Integral property computation is well known to those skilled in the art and so is not discussed here.

Layered manufacturing 562 uses the voxelized data to perform layered manufacturing (e.g., to make prototype models from CAD/CAM created designs). Layered manufacturing is well known to those skilled in the art and so is not discussed here.

Finite element analysis 564 performs finite element analysis (e.g., to calculate failure modes for parts modeled in 3D). Finite element analysis is well known to those skilled in the art and so is not discussed here.

While the invention has been described in conjunction with the preferred embodiments, it should be evident that numerous alternatives, modifications, variations and uses will be apparent to those skilled in the art in light of the foregoing description.

We claim:

1. A method for voxelization of a 3D object in 3D space, the 3D object having a surface, the 3D object represented by a predetermined type of 3D model, the method comprising the steps of:
   a. generating a slice of the 3D object and storing the slice in a frame buffer having blending functions, with each pixel of the frame buffer representing a voxel in the slice, wherein the step of generating the slice includes the steps of:
      I. determining the type of 3D model of the 3D object;
      II. defining a viewing volume comprising at least a portion of the 3D space;
      III. rendering in the frame buffer the surface of any portion of the 3D object found within the viewing volume; and
      IV. applying predetermined frame buffer blending functions associated with the 3D model type of the 3D object to the voxels of each slice stored in the frame buffer;
   b. writing the slice from the frame buffer to a plane location in a 3D memory storage matrix, with the plane location for the slice chosen to maintain the relative position of the slice to the 3D object; and
   c. repeating steps a and b until the entire object has been voxelized.

2. The method of claim 1, wherein the step a(IV) of applying the appropriate frame buffer blending function comprises, for objects determined to be curve/surface 3D model types, the step of generating the slice directly from the surface of any portion of the 3D object found within the viewing volume without applying frame buffer blending functions.

3. The method of claim 1, wherein the step a(IV) of applying the appropriate frame buffer blending function comprises, for 3D objects determined to be boundary/surface 3D model types, the step of applying an XOR blending function to convey between successive slices the status of each voxel in the slice as either inside or outside of the 3D object.

4. The method of claim 1, wherein the step a(IV) of applying the appropriate frame buffer blending function, for objects determined to be Volume Constructive Solid Geometry 3D model types, comprises:
   converting all primitives of the 3D object that are of boundary/surface 3D model type to volumes; and
   for each binary node of the VCSG tree representing the 3D object, when creating the slices in the frame buffer using frame buffer functions to simulate the Boolean operation required at that node.

5. The method of claim 1, wherein the step a(IV) of applying the appropriate frame buffer blending function, for objects determined to be the Generalized Constructive Solid Geometry 3D model type, comprises:
   assigning each primitive composing the object a unique bit location in a color value;
   using the frame buffer hardware pixel map to classify the voxels within the slice as either inside or outside each primitive based on the color value associated with that voxel; and
   using the frame buffer hardware pixel map to classify the voxels within the slice as either inside or outside the object based on the classification of the voxels as either inside or outside each primitive.

6. The method of claim 1, wherein the step of defining a viewing volume comprises the steps of:

defining a bounded cubic volume space over the 3D object;

defining a viewing direction for a 2D image rendered from the 3D object;

defining a projection plane perpendicular to the viewing direction; and defining a first and a second plane, each parallel to the projection plane and intersecting with the boundaries of the cubic volume space, the viewing volume being the portion of the cubic volume space bounded by the first and the second plane;

and wherein the step of writing the slice from the frame buffer comprises the step of:

defining for each slice a plurality of voxels, with each voxel including vertices lying in the first or second planes, each voxel corresponding to a point in the frame buffer.

7. The method of claim 1, wherein the 3D memory storage matrix is located in texture memory.

8. The method of claim 1, wherein the 3D memory storage matrix is located in main memory of a computer system.

9. The method of claim 1, wherein the step c of repeating steps a and b comprises generating successive, adjacent slices of the 3D object.

10. An apparatus for voxelizing a 3D object in 3D space, the 3D object having a surface, the 3D object represented by a predetermined 3D model type, the apparatus comprising:

a frame buffer memory, including a frame buffer having a 2D array of pixels;

a memory having a 3D memory storage matrix coupled to the frame buffer of the frame buffer memory;

a slice generating mechanism coupled to the 3D space and the frame buffer, the slice generating mechanism being operable to generate a series of slices of the 3D object in 3D space by (a) sequentially defining a viewing volume comprising at least a portion of the 3D space, and (b) rendering in the frame buffer the surface of any portion of the 3D object found within the viewing volume, wherein each slice comprises a 2D array of voxels, with each voxel associated with a pixel in the 2D array of pixels in the frame buffer; and a frame buffer blending mechanism, coupled to the frame buffer and the 3D memory storage matrix, the frame buffer blending mechanism capable of transferring a slice stored in the frame buffer to the 3D memory storage matrix while performing one or more predetermined frame buffer blending functions on each slice stored in the frame buffer, with the performance of any frame buffer blending functions a function of the predetermined 3D model type of the 3D object.

11. The apparatus of claim 10, wherein the frame buffer blending mechanism comprises a mechanism to prevent the application of any frame buffer blending functions in transferring a slice when the 3D object is a curve/surface 3D model type.

12. The apparatus of claim 10, wherein the frame buffer blending mechanism comprises a mechanism to apply an XOR frame buffer blending function to the voxels in the slice transferred to the 3D memory storage matrix to convey between successive slices transferred to the 3D memory storage matrix the status of each voxel in the slice as either inside or outside of the 3D object, when the 3D object is of boundary/surface 3D model type.

13. The apparatus of claim 10, wherein the 3D object may be composed of one or more primitives, and each primitive may be of the boundary surface model type or the Volume Constructive Solid Geometry (VCSG) 3D model type and wherein the frame buffer blending mechanism comprises:

a mechanism to convert any primitives of the 3D object that are of boundary/surface 3D model type to volumes; and a mechanism that uses frame buffer blending functions to simulate any Boolean operation required at any binary node of any VCSG tree representing the 3D object.

14. The apparatus of claim 10 wherein the 3D matrix storage memory is texture memory.

15. The apparatus of claim 10, wherein the 3D matrix storage memory is main memory in a computer system.

16. A method for voxelization of a generalized Constructive Solid Geometry (CSG) model of an object in 3D space, the 3D space including a plurality of coordinate points, the object composed of a plurality of primitives, the generalized CSG model including a generalized CSG tree having a lowest level consisting of a leaf node associated with each primitive of the object, each leaf node acting as a child node, at least one binary node associated with two child nodes at a level below the binary node, with each binary node including an associated Boolean operation that governs the interaction between its associated child nodes, each child node associated with only a single binary node above, a leaf node formed by the binary node at the highest level of the CSG tree and composed of two child nodes below, and each binary node other than the leaf node forming a child node for a binary node above, comprising the steps of:

converting the generalized CSG model into a binary 3D model of the object, including the steps of:

for each coordinate point in 3D space, creating a classification index for the point indicative of whether the point is interior to or exterior to each primitive;

for each primitive, creating a point classification map that maps each classification index against the primitive and its associated child node of the CSG tree;

for each child node, determining a point classification map for its associated binary node based on the child node's point classification map, the point classification map of the other child node associated with its binary node, and the Boolean operation associated with the binary node;

for each binary node, determining a point classification map for its associated binary node above based on the binary node's point classification map, the point classification map of the other node associated with the binary node above, and the Boolean operation associated with the binary node above; and recursively determining the point classification maps for binary nodes until the point classification map is determined for the leaf node; and voxelizing the binary 3D model of the object.

17. The method of claim 16, wherein the step of creating a point classification map for each coordinate point includes the step of assigning an n-bit word to each point, where "n" is the number of primitives comprising the object, where each primitive is assigned a unique one of the bits of the n-bit word, and the value in each bit represents whether or not the particular primitive contains the particular point to which the n-bit word is assigned.

18. The method of claim 17, wherein the coordinate points in the 3D object space are first defined by the steps comprising:

defining a cubic volume space over the object;

defining a viewing direction for a 2D image rendered from the 3D object;

defining a projection plane perpendicular to the viewing direction;

defining one or more slices in the cubic volume space, each slice defined by the intersection of the boundaries of the cubic volume space with a first and a second plane, each parallel to the projection plane; and defining for each slice a plurality of voxels, with each voxel including vertices lying in the first or second planes, the voxel vertices forming the coordinate points.

19. A method for voxelization of a generalized CSG model of an object in 3D space using a computer system, the computer system including a frame buffer and texture memory, the 3D space including a plurality of coordinate points, the object composed of a plurality of primitives, the generalized CSG model including a generalized CSG tree having a lowest level consisting of a child node associated with each primitive of the object, at least one binary node associated with two child nodes at a level below, with each binary node including an associated Boolean operation that governs the interaction between its associated child nodes, each child node associated with only a single binary node above, a leaf node formed by the binary node at the highest level of the CSG tree and composed of two child nodes below, and each binary node other than the leaf node forming a child node for a binary node above, comprising the steps of:

converting the generalized CSG model into a binary 3D model of the object, including the steps of:

for each coordinate point in 3D space, creating a classification index in the frame buffer for the point indicative of whether the point is interior to or exterior to each primitive;

for each primitive, creating a point classification map in the frame buffer that maps each classification index in the frame buffer against the primitive and its associated child node of the CSG tree;

for each child node, determining a point classification map in the frame buffer for its associated binary node based on the child node's point classification map, the point classification map of the other child node associated with its binary node, and the Boolean operation associated with the binary node;

for each binary node, determining a point classification map in the frame buffer for its associated binary node above based on the binary node's point classification map, the point classification map of the other node associated with the binary node above, and the Boolean operation associated with the binary node above; and recursively determining the point classification maps for binary nodes until the point classification map in the frame buffer is determined for the leaf node; and voxelizing the binary 3D model of the object; and moving the point classification map for the leaf node into the texture memory.

20. The method of claim 19, wherein the frame buffer includes an n-bit color value word associated with each pixel in the frame buffer and the step of creating a point classification map for each coordinate point, including the step of assigning an n-bit word in the frame buffer to each point, where "n" is the number of primitives comprising the object, n is less than m, with each primitive is associated a unique one of the bits of the n-bit word, the value in each bit represents whether or not the particular primitive contains the particular point to which the n-bit word is assigned.

* * * * *